United States Patent
Lewicke et al.

(10) Patent No.: US 8,801,636 B2
(45) Date of Patent: Aug. 12, 2014

(54) METHOD AND APPARATUS FOR DETERMINING WELLNESS BASED ON DECUBITUS POSTURE

(75) Inventors: Aaron Lewicke, Forest Lake, MN (US); John D. Hatlestad, Maplewood, MN (US); Abhilash Patangay, Inver Grove Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 190 days.

(21) Appl. No.: 11/780,411

(22) Filed: Jul. 19, 2007

(65) Prior Publication Data

US 2009/0024005 A1    Jan. 22, 2009

(51) Int. Cl.
*A61B 5/02* (2006.01)
*A61B 5/11* (2006.01)
*A61B 5/00* (2006.01)

(52) U.S. Cl.
CPC ............... *A61B 5/1112* (2013.01); *A61B 5/686* (2013.01)
USPC .......................................... 600/595; 600/301

(58) Field of Classification Search
USPC ....................................................... 600/595
See application file for complete search history.

(56) References Cited

U.S. PATENT DOCUMENTS

| | | | |
|---|---|---|---|
| 4,617,525 A * | 10/1986 | Lloyd | 340/573.1 |
| 4,860,751 A | 8/1989 | Callaghan | |
| 5,038,137 A * | 8/1991 | Lloyd | 340/573.7 |
| 5,040,536 A | 8/1991 | Riff | |
| 5,354,317 A | 10/1994 | Alt | |
| 5,472,453 A | 12/1995 | Alt | |
| 5,593,431 A * | 1/1997 | Sheldon | 607/19 |
| 5,833,603 A | 11/1998 | Kovacs et al. | |
| 5,957,957 A | 9/1999 | Sheldon | |
| 6,002,963 A | 12/1999 | Mouchawar et al. | |
| 6,044,297 A | 3/2000 | Sheldon et al. | |
| 6,104,949 A | 8/2000 | Pitts Crick et al. | |
| 6,135,970 A | 10/2000 | Kadhiresan et al. | |
| 6,334,063 B1 | 12/2001 | Charlier et al. | |
| 6,616,607 B2 | 9/2003 | Hashimoto et al. | |
| 6,658,292 B2 | 12/2003 | Kroll et al. | |
| 6,662,047 B2 | 12/2003 | Sorensen et al. | |

(Continued)

FOREIGN PATENT DOCUMENTS

| | | |
|---|---|---|
| EP | 1115350 B1 | 8/2003 |
| JP | 2006-204742 A | 8/2006 |

(Continued)

OTHER PUBLICATIONS

Leung et al. "Avoidance of the Left Lateral Decubitus Position During Sleep in Patients with Heart Failure: Relationship to Cardiac Size and Function" Journal of the Americal College of Cardiology Vo. 41, No. 2, 2003.*

(Continued)

*Primary Examiner* — Sean Dougherty
*Assistant Examiner* — Michael C Stout
(74) *Attorney, Agent, or Firm* — Schwegman, Lundberg & Woessner, P.A.

(57) ABSTRACT

An example method includes monitoring a first posture including a first lateral decubitus posture (LDP), recording a first LDP record based on the first LDP, computing a first posture trend based on the first LDP record and determining and providing a wellness indication based on the first posture trend.

29 Claims, 13 Drawing Sheets

(56) References Cited

U.S. PATENT DOCUMENTS

| | | | |
|---|---|---|---|
| 6,692,446 B2 | 2/2004 | Hoek | |
| 6,937,900 B1 | 8/2005 | Pianca et al. | |
| 7,226,422 B2 * | 6/2007 | Hatlestsad et al. | 600/534 |
| 7,308,309 B1 * | 12/2007 | Koh | 607/17 |
| 8,065,001 B1 * | 11/2011 | Nabutovsky et al. | 607/17 |
| 8,282,580 B2 * | 10/2012 | Skelton et al. | 600/595 |
| 2004/0073093 A1 | 4/2004 | Hatlestad | |
| 2004/0073128 A1 * | 4/2004 | Hatlestad et al. | 600/533 |
| 2004/0106962 A1 | 6/2004 | Mai et al. | |
| 2004/0127790 A1 * | 7/2004 | Lang et al. | 600/438 |
| 2004/0215263 A1 | 10/2004 | Virag et al. | |
| 2004/0267330 A1 * | 12/2004 | Lee et al. | 607/48 |
| 2005/0113646 A1 * | 5/2005 | Sotos et al. | 600/300 |
| 2005/0115561 A1 * | 6/2005 | Stahmann et al. | 128/200.24 |
| 2005/0145246 A1 * | 7/2005 | Hartley et al. | 128/203.14 |
| 2005/0216067 A1 * | 9/2005 | Min et al. | 607/17 |
| 2005/0234514 A1 * | 10/2005 | Heruth et al. | 607/2 |
| 2006/0017575 A1 * | 1/2006 | McAdams | 340/573.1 |
| 2006/0025699 A1 | 2/2006 | Maile et al. | |
| 2006/0030892 A1 * | 2/2006 | Kadhiresan et al. | 607/19 |
| 2006/0041280 A1 | 2/2006 | Stahmann et al. | |
| 2006/0064136 A1 * | 3/2006 | Wang | 607/27 |
| 2006/0161070 A1 * | 7/2006 | Siejko et al. | 600/528 |
| 2006/0173257 A1 * | 8/2006 | Nagai et al. | 600/323 |
| 2006/0190051 A1 * | 8/2006 | Gerber et al. | 607/41 |
| 2006/0195149 A1 * | 8/2006 | Hopper et al. | 607/11 |
| 2006/0224190 A1 * | 10/2006 | Gill et al. | 607/3 |
| 2006/0235302 A1 * | 10/2006 | Grossman et al. | 600/443 |
| 2006/0253006 A1 * | 11/2006 | Bardy | 600/300 |
| 2006/0276848 A1 * | 12/2006 | Min et al. | 607/17 |
| 2007/0015976 A1 * | 1/2007 | Miesel et al. | 600/301 |
| 2007/0021678 A1 * | 1/2007 | Beck et al. | 600/510 |
| 2007/0032733 A1 * | 2/2007 | Burton | 600/509 |
| 2007/0115277 A1 * | 5/2007 | Wang et al. | 345/419 |
| 2007/0118056 A1 * | 5/2007 | Wang et al. | 600/595 |
| 2007/0123953 A1 * | 5/2007 | Lee et al. | 607/48 |
| 2007/0129641 A1 * | 6/2007 | Sweeney | 600/513 |
| 2007/0129643 A1 * | 6/2007 | Kwok et al. | 600/529 |
| 2007/0129774 A1 * | 6/2007 | Bourget et al. | 607/62 |
| 2007/0142733 A1 * | 6/2007 | Hatlestad et al. | 600/508 |
| 2007/0150026 A1 * | 6/2007 | Bourget et al. | 607/46 |
| 2007/0150029 A1 * | 6/2007 | Bourget et al. | 607/62 |
| 2007/0156057 A1 * | 7/2007 | Cho et al. | 600/513 |
| 2007/0161912 A1 * | 7/2007 | Zhang et al. | 600/483 |
| 2007/0249968 A1 * | 10/2007 | Miesel et al. | 600/595 |
| 2008/0082001 A1 * | 4/2008 | Hatlestad et al. | 600/481 |
| 2008/0269812 A1 * | 10/2008 | Gerber et al. | 607/2 |
| 2008/0269843 A1 * | 10/2008 | Gerber et al. | 607/62 |
| 2008/0300641 A1 * | 12/2008 | Brunekreeft et al. | 607/6 |
| 2009/0024005 A1 * | 1/2009 | Lewicke et al. | 600/301 |
| 2009/0048538 A1 | 2/2009 | Levine et al. | |
| 2009/0105785 A1 * | 4/2009 | Wei et al. | 607/48 |
| 2009/0112289 A1 * | 4/2009 | Lee et al. | 607/59 |
| 2009/0234200 A1 * | 9/2009 | Husheer | 600/301 |
| 2010/0113961 A1 * | 5/2010 | Ohlander et al. | 600/547 |
| 2010/0217135 A1 * | 8/2010 | Cho et al. | 600/485 |

FOREIGN PATENT DOCUMENTS

| | | |
|---|---|---|
| WO | WO-2005046472 A1 | 5/2005 |
| WO | WO 2006/078757 A1 | 7/2006 |
| WO | WO-2007/061746 A2 | 5/2007 |
| WO | WO-2009/011886 A1 | 1/2009 |

OTHER PUBLICATIONS

Miyamoto et al. "Effects of Posture on Cardiac Autonomic Nervous Activity in Patients with Congestive Heart Failure," Journal of American College of Cardiology vol. 37 No. 7, 2001.*

"International Application Serial No. PCT/US2008/008738, International Search Report mailed Nov. 4, 2008", 4 pgs.

"International Application Serial No. PCT/US2008/008738, Written Opinion mailed Nov. 4, 2008", 7 pgs.

Miyamato, S., et al., "Effects of Posture on Cardiac Activity in Patients With Congestive Heart Failure," *Journal of the American College of Cardiology*, 37(7), (2001), 1788-1793.

Fujita, M., et al., "Effects of Posture on Sympathetic Nervous Modulation in Patients With Chronic Heart Failure", *The Lancet*, 356(9244), (Nov. 25, 2000), 1822-1823.

Hatlestad, J. D., et al., "Physiological Response to Posture Change", U.S. Appl. No. 11/466,925, filed Aug. 24, 2006, 21 Pages.

Hatlestsad, J., et al., "Detection of Congestion From Monitoring Patient Response to a Recumbent Position", U.S. Appl. No. 11/619,821, filed Jan. 4, 2007, 27 pgs.

Leung, R., et al., "Avoidance of the Left Lateral Decubitus Position During Sleep in Patients With Heart Failure: Relationship to Cardiac Size and Function", *Journal of the American College of Cardiology*, 41(2), (Jan. 15, 2003), 227-230.

Levine, T. B., et al., "The Neurohumoral and Hemodynamic Response to Orthostatic Tilt in Patients with Congestive Heart Failure", *Circulation*, 67(5), (May 1983), 1070-1075.

Miyamoto, S., "Effects of Posture on Cardiac Autonomic Nervous Activity in Patients with Congestive Heart Failure", *Journal of the American College of Cardiology*, 37(7), (Jun. 1, 2001),1788-1793.

Palermo, P., et al., "Lateral Decubitus Position Generates Discomfort and Worsens Lung Function in Chronic Heart Failure", *Chest*, 128, (2005),1511-1516.

Sweeney, R. J., "Posture Estimation at Transitions Between States", U.S. Appl. No. 11/291,479, filed Dec. 1, 2005, 22 Pages.

"Australian Application Serial No. 2008276527, Response filed Aug. 31, 2011 to Examiner Report dated Nov. 22, 2010", 19 pgs.

"Australian Application Serial No. 2008276527, First Examiner Report mailed Nov. 22, 2010", 7 pgs.

"Chinese Application Serial No. 200880106610.2, Office Action mailed Apr. 19, 2011", (w/English Translation), 7 pgs.

"Chinese Application Serial No. 200880106610.2, Response filed Aug. 12, 2011 to Office Action mailed Apr. 19, 2011", (w/ English Translation of Claims), 16 pgs.

"Chinese Application Serial No. 200880106610.2, Office Action mailed Apr. 1, 2012", (w/ English Translation), 8 pgs.

"Chinese Application Serial No. 2008801066102, Response filed Jun. 4, 2012 to Office Action mailed Apr. 1, 2012", (w/ English Translation of Claims), 9 pgs.

"International Application U.S. Appl. No. PCT/US2008/008738, International Preliminary Report on Patentability mailed Jan. 28, 2010", 7 pgs.

"Japanese Application Serial No. 2010-517016, Office Action mailed Apr. 10, 2012", (w/ English Translation), 4 pgs.

"Japanese Application Serial No. 2010-517016, Response filed Jul. 9, 2012 to Office Action mailed Apr. 10, 2012", (w/ English Translation of Amended Claims), 10 pgs.

"Chinese Application Serial No. 200880106610.2, Response filed Dec. 21, 2012 to Office Action mailed Oct. 29, 2012", English Claims, 8 pgs.

"Chinese Application Serial No. 20880106610.2, Office Action mailed Oct. 29, 2012", With English Translation, 7 pgs.

"European Application Serial No. 08794550.7, Examination Notification Art. 94(3) mailed Nov. 28, 2013", 4 pgs.

* cited by examiner

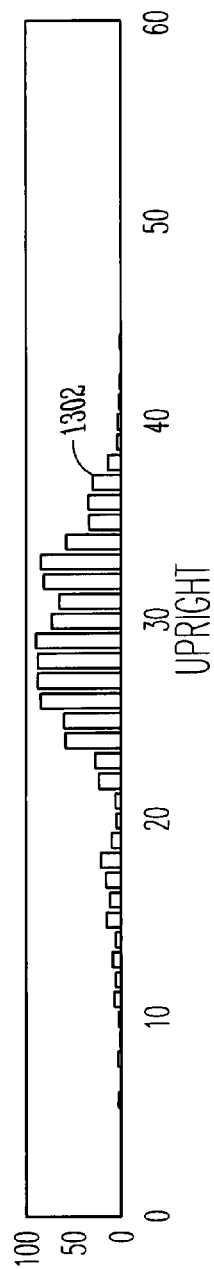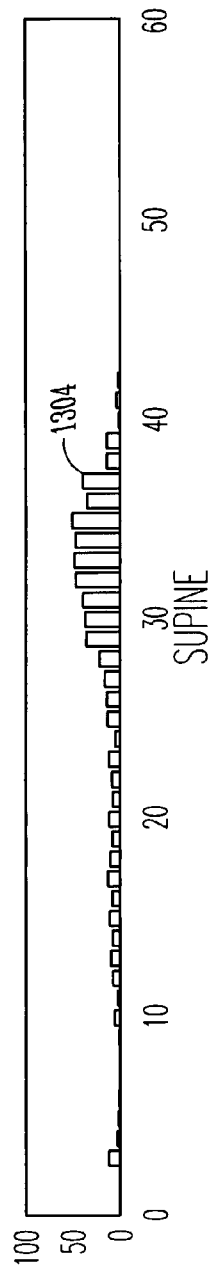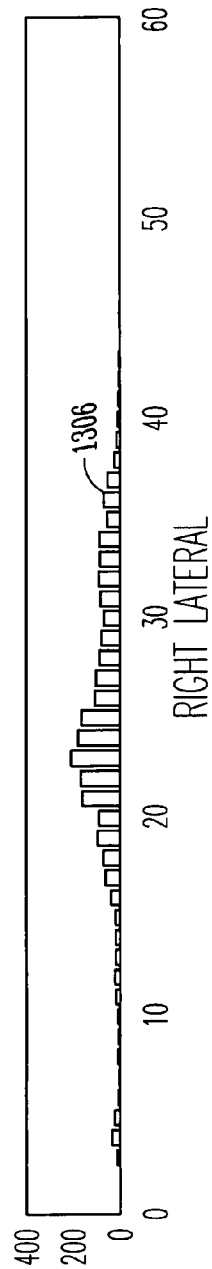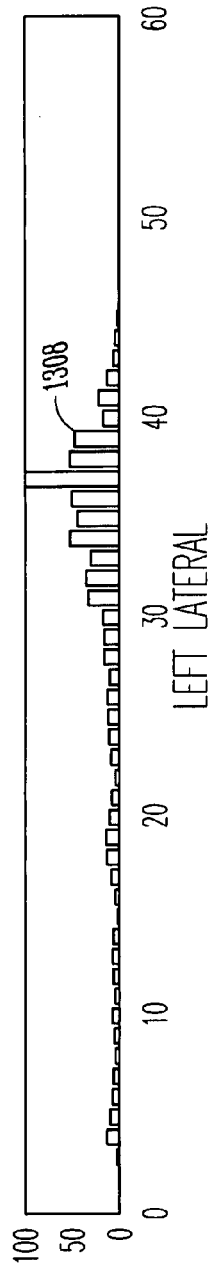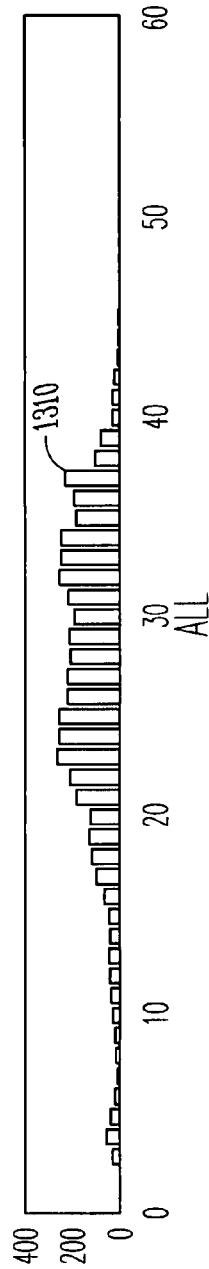
Fig. 13

METHOD AND APPARATUS FOR DETERMINING WELLNESS BASED ON DECUBITUS POSTURE

TECHNOLOGY FIELD

This document pertains to posture measurement systems and particularly, but not by way of limitation, to method and apparatus for determining wellness based on decubitus posture.

BACKGROUND

A person's health status can be determined by analyzing physiological indications including, but not limited to, heart rate, respiration pattern, blood pressure, etc. One or more of these physiological indications follow different trends for an unwell person than for a well person. Measuring and trending one or more physiological indications can provide useful information about a person's state of wellness.

OVERVIEW

The present inventors have recognized, among other things, that when a patient assumes a decubitus posture versus other postures, their wellness can be influenced. Information about which decubitus posture is assumed, or how it affects the body, can be used to diagnose or treat diseases or disorders. The present inventors have also recognized that in some cases a patient will preferentially assume a decubitus posture over another posture. If a patient exhibits such behavior, this phenomenon can be recorded and used to provide an indication of patient wellness. The present inventors have recognized that such techniques can be combined with techniques that monitor physiological trend information (e.g., blood pressure, cardiac output, pulmonary fluid level, etc.) to provide even more information about diseases and disorders. The devices and methods discussed here include tools for monitoring such information and for treating a patient based on this information. Several examples are provided.

In Example 1, a method includes monitoring a first posture including a first lateral decubitus posture (LDP), recording a first LDP record based on the first LDP, computing a first posture trend based on the first LDP record and determining and providing a wellness indication based on the first posture trend.

In Example 2, the method of Example 1 is optionally configured to include detecting a physiological indication other than posture and computing the wellness indication also based on the physiological indication.

In Example 3, the method of one or more of Examples 1-2 is optionally configured such that the wellness indication includes an actual or potential heart failure indication.

In Example 4, the method of one or more of Examples 1-3 is optionally configured such that the first posture trend is recorded over one circadian rhythm period.

In Example 5, the method of one or more of Examples 1-4 is configured to optionally include recording a second posture differing from the first LDP computing a second posture trend based on the second posture and determining and providing the wellness indication based on the first posture trend and the second posture trend.

In Example 6, the method of one or more of Examples 1-5 is configured to optionally include comparing the first posture trend to the second posture trend and determining and providing the wellness indication based on the comparison of the first posture trend and the second posture trend.

In Example 7, the method of one or more of Examples 1-6 is optionally configured such that the first posture includes a right lateral decubitus posture (RLDP), and the second posture includes a left lateral decubitus posture (LLDP).

In Example 8, the method of one or more of Examples 1-7 is optionally configured such that the second posture includes at least one of a supine posture or a prone posture.

In Example 9, the method of one or more of Examples 1-8 is configured to optionally include providing an alert when the wellness indication includes a decreased wellness indication.

In Example 10, the method of one or more of Examples 1-9 is configured to optionally include recording a second posture differing from the first LDP, computing the wellness indication based on the first posture and the second posture, the wellness indication including a first wellness level based on the first posture and a second wellness level based on the second posture, comparing the first wellness level and the second wellness level to determine a third posture associated with increased wellness over the first and second postures and providing an indication of the third posture.

In Example 11, the method of one or more of Examples 1-10 is optionally configured such that the third posture includes a supine tilt posture.

In Example 12, an apparatus is configured to include a posture sensor configured to produce a first posture indication including a first lateral decubitus posture (LDP), a posture memory circuit coupled to the posture sensor, the posture memory circuit configured to store a first LDP record based on the first posture indication, a posture trend circuit coupled to the posture memory circuit, the posture trend circuit configured to produce a posture trend based on the first LDP record and a wellness indicator circuit coupled to the posture trend circuit, the wellness indicator circuit configured to compute and provide a wellness indication based on the posture trend.

In Example 13, the apparatus of Example 12 is optionally configured such that the first LDP is a left lateral decubitus posture (LLDP), the posture sensor is configured to produce a second posture indication include a right lateral decubitus posture (RLDP), the posture memory circuit is configured to store an RLDP record based on the second posture indication, and the posture trend circuit is configured to produce the posture trend based on a comparison of the first LDP record and the RLDP record.

In Example 14, the apparatus of one or more of Examples 12-13 is optionally configured such that the posture sensor is implantable.

In Example 15, the apparatus of one or more of Examples 12-14 is optionally configured such that the posture sensor is configured to produce a second posture indication including at least one of a supine posture or a prone posture, the posture memory circuit is configured to store a supine record and a prone record, the prone record and the supine record based on the second posture indication, and the posture trend circuit is configured to produce the posture trend based on a comparison of the first LDP record, the supine record and the prone record.

In Example 16, the apparatus of one or more of Examples 12-15 is optionally configured such that the wellness indicator circuit is configured to compare the posture trend to a specified posture trend.

In Example 17, the apparatus of one or more of Examples 12-16 is configured to optionally include an alert circuit communicatively coupled to the wellness indicator circuit, the alert circuit configured to trigger an alert when the wellness indication includes a decreased wellness indication.

In Example 18, the apparatus of one or more of Examples 12-17 is optionally configured such that the alert includes at least one of an email message, a phone call, a flashing light, a mattress tilt adjustment signal, a mattress temperature adjustment signal, a mattress firmness adjustment signal, or an audible tone.

In Example 19, the apparatus of one or more of Examples 12-18 is configured to optionally include an electrical pulse circuit coupled to the alert circuit, the electrical pulse circuit configured to provide an electrical pulse based on the alert.

In Example 20, the apparatus of one or more of Examples 12-19 is optionally configured such that the electrical pulse circuit is configured to produce at least one of a premature ventricular complex (PVC), an intermittent diaphragm stimulation, or an uncomfortable electric shock.

In Example 21, the apparatus of one or more of Examples 12-20 is configured to optionally include a physiologic sensor configured to produce a physiologic indication other than posture, a physiologic indication memory, coupled to the physiologic sensor, the physiologic indication memory configured to store a physiologic indication record based on the physiology indication and a physiologic indication trend circuit coupled to the physiologic indication memory circuit, the physiologic indication trend circuit configured to produce a physiologic indication trend based on the physiologic indication record. Example 21 is optionally configured such that the wellness circuit is configured to compute the wellness indication based on the physiologic record.

In Example 22, the apparatus of one or more of Examples 12-21 is optionally configured such that the physiologic sensor includes, and uses for forming the physiologic indication, at least one of an autonomic balance sensor, a breath sensor, an pulmonary fluid sensor, a cardiac output sensor, a preload circuit, a weight change sensor, a pressure sensor, a heart rate sensor, a heart rate variability sensor, or a heart sounds sensor.

In Example 23, the apparatus of one or more of Examples 12-22 is optionally configured such that the autonomic balance sensor includes a heart rate variability power spectrum comparator configured to produce a ratio of low frequency autonomic activity to high frequency autonomic activity.

In Example 24, the apparatus of one or more of Examples 12-23 is optionally configured such that the physiologic indication includes at least one of a paroxysmal nocturnal dyspnea indication or an orthopnea indication.

In Example 25, a system for monitoring a patient includes means for monitoring patient posture, means for recording a lateral decubitus posture (LDP), means for computing a posture trend based on the LDP and means for determining and providing a wellness indication based on the posture trend.

In Example 26, the system of Example 25 is optionally configured such that the means for monitoring patient posture include a posture sensor configured to produce a first posture indication including a lateral decubitus posture (LDP).

In Example 27, the system of one or more of Examples 25-26 is optionally configured such that the means for recording a lateral decubitus posture (LDP) include a posture memory circuit coupled to the posture sensor, the posture memory circuit configured to store an LDP record based on the first posture indication.

In Example 28, the system of one or more of Examples 25-27 is optionally configured such that the means for computing a posture trend based on the LDP include a posture trend circuit coupled to the posture memory circuit, the posture trend circuit configured to produce a posture trend based on the LDP record.

In Example 29, the system of one or more of Examples 25-28 is optionally configured such that the means for determining a wellness indication based on the posture trend include a wellness indicator circuit coupled to the posture trend circuit, the wellness indicator circuit configured to compute and provide a wellness indication based on the posture trend.

This Overview is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of that are not to be taken in a limiting sense. The scope of the present invention is defined by the appended claims and their equivalents.

DESCRIPTION OF THE DRAWINGS

FIG. 13 illustrates data recorded for diagnosis, according to some examples.

DETAILED DESCRIPTION

This document discusses examples of systems and methods of monitoring lateral decubitis posture, such as to determine an indication or alert of patient wellness status, to initiate or adjust a therapy, or to help the patient use a particular posture that is believed beneficial with respect to heart failure, or to avoid a particular posture that is believed detrimental with respect to heart failure.

In a lateral decubitus posture, a patient is lying on his or her side such as on a surface, e.g., either perpendicular to the surface or even not exactly perpendicular to that surface. Without being bound by theory, it is believed that heart failure patients tend to increasingly prefer the right lateral decubitis posture as their heart failure condition worsens. Similarly, without being bound by theory, it is believed that heart failure patients tend to increasingly avoid the left lateral decubitis posture as the heart failure condition worsens. Furthermore, without being bound by theory, it is believed that heart failure patients tend to increasingly prefer an increasing upward recumbent tilt as the heart failure condition worsens—particularly in the later stages of heart failure decompensation as pulmonary edema (fluid accumulation in the lungs) begins to occur.

Figure 1:
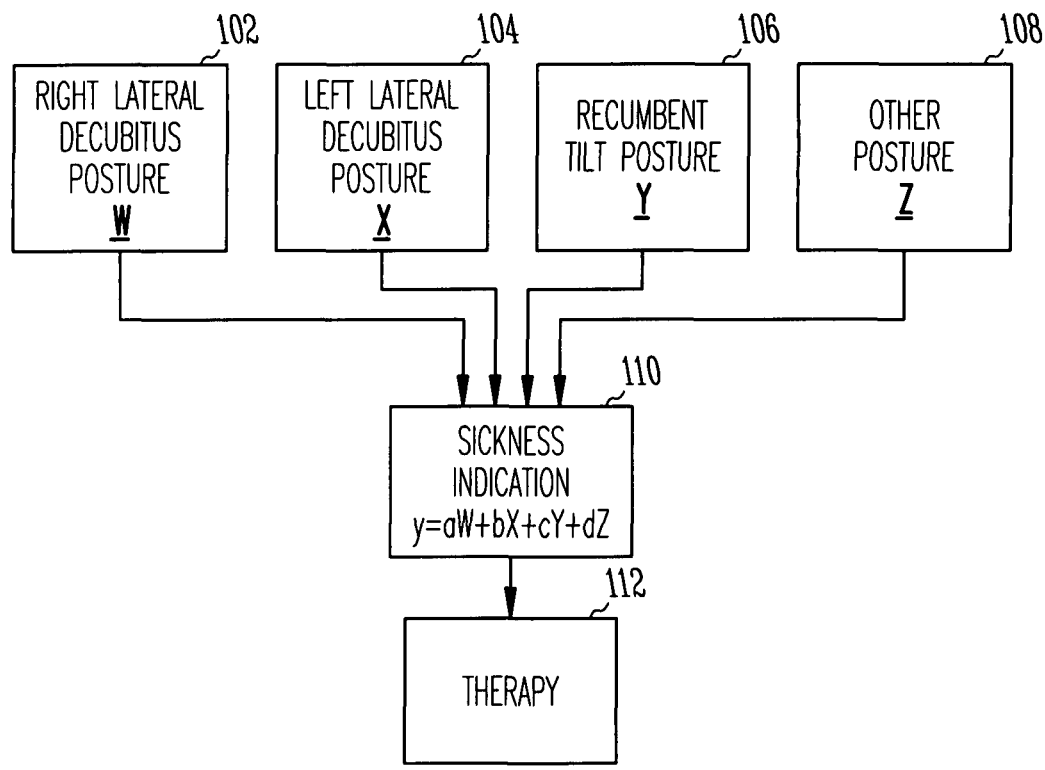
FIG. 1 illustrates a method that includes diagnosing a sickness, according to some examples.

In certain examples, the present systems and methods use decubitus posture information to provide heart failure status or another wellness indicator. FIG. 1 illustrates a method that includes diagnosing a sickness, according to some examples. The method is capable of monitoring whether a patient is preferentially assuming or not assuming a decubitus posture or any other posture. A right lateral decubitus indication W is recorded, at 102, which at least represents how much time a patient has spent in the right lateral decubitus posture. A left lateral decubitus indication X is recorded, at 104, which at least represents how much time a patient has spent in the left lateral decubitus posture. A recumbent tilt posture indication Y is recorded, at 106, which at least represents how much time a patient has spent in a recumbent tilt posture. Another posture indication Z is recorded, at 108, which represents at least how much time a patient has spent out of the left and right decubitus postures, as well as out of a recumbent tilt posture. These indications can optionally aggregate information about degree of tilt. For example, measurement W can weight time spent in the right lateral decubitus posture based on angles assumed with respect to a surface. If the right lateral decubitus posture is assumed as intended, the weight would be 1. A lesser weight could be assigned for postures that are close to an intended right lateral decubitus posture, but vary slightly (e.g., due to a patient lying on a pillow).

These indications are used alone or in combination to provide, at 110, a sickness indication. The sickness indication y, in various examples, collects indications 102-108 and optionally weights them according to a specified weighting scheme. The weighting scheme can include the example represented by Equation (1).

$$y = aW + bX + cY + dZ \quad (1)$$

If a weighting scheme seeks only to provide a sickness indication that monitors the amount of time spent in a right lateral decubitus posture versus the amount of time spent in the left lateral decubitus posture, the example can assign a weight of 1 to variables a, b and a weight of zero to the remaining variables. If the example seeks to provide a diagnosis based on a combination of any of the indications, variables a, b, c, and d can be weighted to 1. If the example foremost wishes to provide a sickness indication y based on time spent in a recumbent tilt posture, and is secondarily interested on providing an indication based on time spent in the right and left lateral decubitus postures, variable c can be weighted greater than variables a and b. In some examples, variable c is greater than variable b, which is greater than variable a. An example of such a scheme is provided in discussion associated with FIG. 2, moreover, in certain examples, a non-linear combination weighting scheme can be used, if desired.

The sickness indication can be used to diagnose patient wellness. The sickness indication can be provided to a physician, a device, or another implement associated with providing patient care. In some examples, sickness can be detected by measuring the amount of time a patient remains in a particular posture and comparing that time to a specified time value. Some examples determine the amount of time spent in a variety of postures, and if there is a trend showing an abnormal postural preference, e.g., when compared to a specified trend (e.g., the behavior of the patient when they are well, or the behavior of an example person from a healthy population), that postural preference can be used to indicate sickness level. In some examples, physicians can use the sickness indication to prescribe a therapy of assuming a posture that improves wellness. This can include prescribing that a patient spends time in a right lateral decubitus posture if doing so improves their health. In some examples, a physician or a device will use the sickness indication to provide therapy 112 to the patient. For example, if the sickness indication shows that the patient is assuming a right lateral decubitus posture in high proportion to other postures, an implanted device can deduce that the patient is suffering from heart failure, and administer a therapy to treat the heart failure. Such therapy can be administered automatically. Such therapy can be in a feedback relationship with the sickness indication y, or it can be in an open loop relationship with sickness indication y, for example, using a trigger signal based on the sickness indication y.

Figure 2:
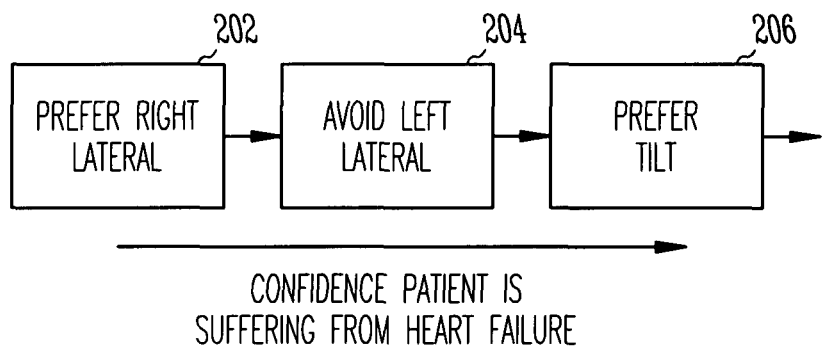
FIG. 2 illustrates a method that includes diagnosing a disease, according to some examples.

FIG. 2 illustrates a method that includes diagnosing a disease, according to some examples. In this example, at 202, posture data is recorded such as to determine whether a patient prefers a right lateral decubitus posture and is spending a significant amount of time in a right lateral decubitus posture. The method can also include, at 204, monitoring whether a patient prefers to avoid the left lateral decubitus posture and is not spending a significant amount of time in the left lateral decubitus posture. The method can include, at 206, determining whether a patient prefers a tilted recumbent posture and is spending a significant amount of time in such a posture. Time amounts reaching significance vary between examples. In some examples, time spent in a particular posture can be compared to time spent in one or more other postures. In additional examples, time spent in a particular posture can be compared to a specified value. Specified values can include those that are preprogrammed or based on a knowledge of phenomena related to diseases or disorders. Such specified values can be those prescribed by a physician to treat an individual, or optionally values demonstrating a particular statistical significance. Other specified values, or figures or merit, can be used.

Some examples provide an indicator of how far a patient has progressed from a state showing no preference for a posture, to showing a preference for a tilted recumbent posture, at 206. In certain examples, the indicator includes or uses information about the time sequence in which the patient exhibits two or more of the preferences 202, 204, or 206. In certain examples, the particular preference 202, 204, or 206 provides a sequence representing an increasing confidence of heart failure or another condition. Heart failure is one of the diseases or disorders that can be diagnosed using the posture preference information. Other indications can also be used in making the heart failure diagnosis, such as respiratory distress, congestion level, etc.

A sickness or wellness or confidence indication can be used to indicate a potential disease or disorder based on collected information so that a care provider can perform further investigation. Some examples collect enough information to indicate a disease or disorder without requiring further investigation by the care provider. As discussed above, some examples collect enough information to confidently begin to administer therapy automatically.

Wellness relates to patient health, and can include information about any diseases or disorders from which a patient might be suffering. Various examples perform a short-term diagnosis of wellness (such as during a clinical visit), or collect data over a long time period (e.g. time periods not compatible with outpatient measurement). Some examples include one or more postures recorded over at least one circadian rhythm period. As such, various examples can monitor a patient from an unwell state to an improved state, and vice-versa.

The examples discussed here can determine wellness using various techniques. In certain examples, wellness is determined by comparing one or more monitored physiological indicators (e.g., autonomic balance, respiration, pulmonary fluid, cardiac output, preload, weight change, vascular pressure, heart rate, heart rate variability and heart sounds) to specified values that represent a well person assuming a certain posture. In some examples, wellness can be diagnosed by comparing one or more physiological indicators detected in a first posture to one or more physiological indicators detected in a second posture. These examples can compare actual results to expected results that are specified.

Figure 3:
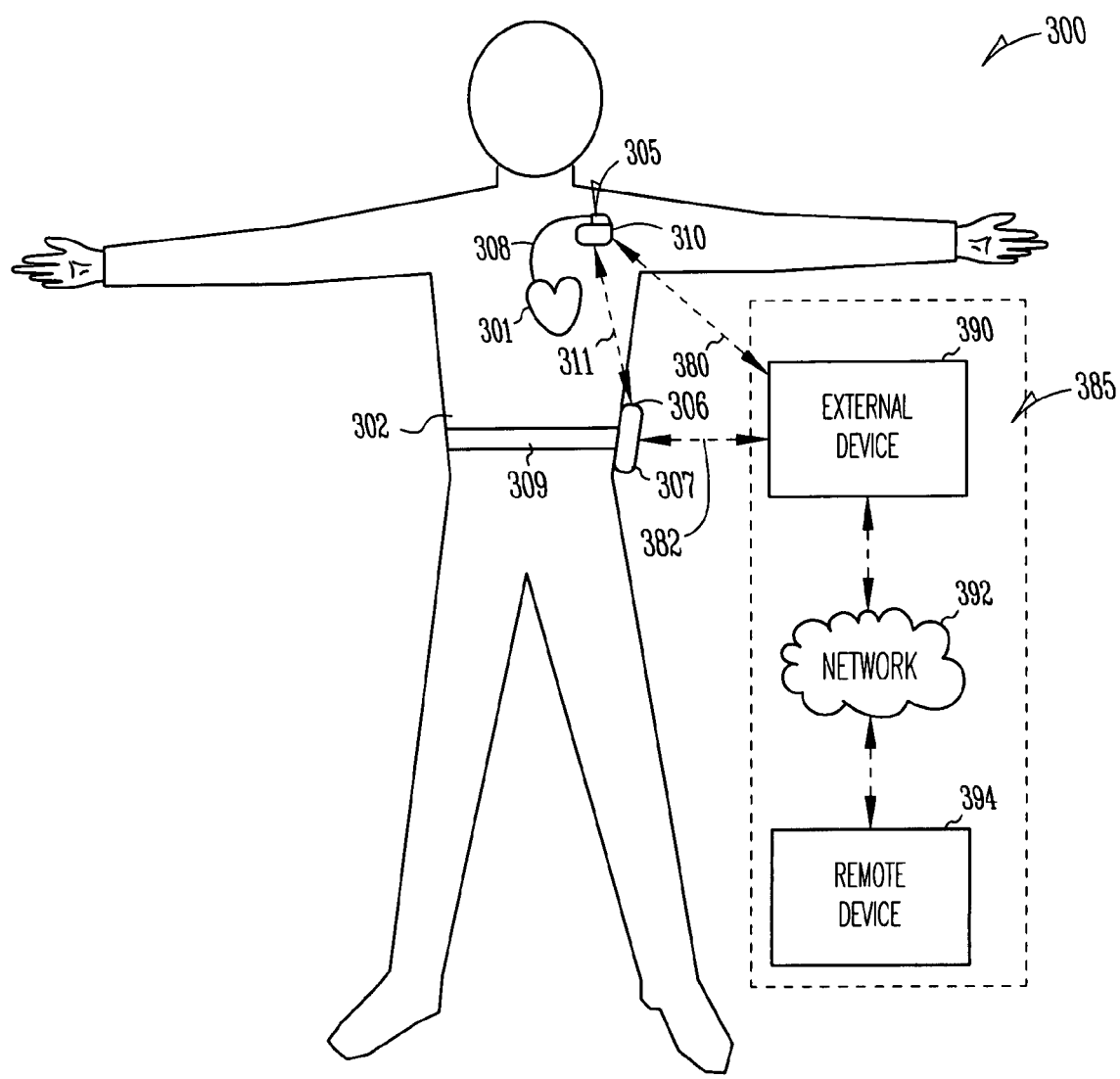
FIG. 3 illustrates a system for posture sensing and portions of an environment in which posture sensing occurs, according to some examples.

FIG. 3 illustrates of an example of a system 300 and portions of an environment in which system 300 is used. In this example, three subsystems are illustrated: an implantable subsystem 305, an externally wearable subsystem 307, and an external subsystem 385. Each of subsystems 305 and 307 can be used separately or in combination with each other. Subsystem 385 is paired with one or both of subsystems 305 and 307, such as to use information gathered by one or both of those subsystems.

Implantable subsystem 305 can include multiple components. One or more of those components are implanted, in certain examples. Certain examples use an implantable case, such as a biocompatible hermetically sealed case.

Some examples use implantable subsystem 305, external subsystem 385, and a telemetry link 380 for providing communication between the implantable subsystem 305 and the external subsystem 385. Some examples include an externally wearable subsystem 307 and a telemetry link 382, which provides for communication between the externally wearable subsystem 307 and the external subsystem 385. In some examples, implantable subsystem 305 and externally wearable subsystem 307 are in telemetric communication 311.

Implantable subsystem 305 can include, among other things, an implantable medical device 310 and a lead system 308, in various examples. In certain examples, the implantable medical device 310 includes a CRM device including one or more of a pacer, a cardioverter/defibrillator, a cardiac resynchronization therapy (CRT) device, a cardiac remodeling control therapy (RCT) device, a neurostimulator, a drug delivery device or a drug delivery controller, or a biological therapy device.

In the example of FIG. 3, implantable medical device 310 is implanted in a body 302. In various examples, electrode or lead system 308 includes one or more implantable electrodes or sensors, such as for sensing physiological signals (e.g. heart rate), such as from one or more locations within, near, or even some distance away from the heart. Lead system 308 can include one or more implantable electrodes for delivering pacing pulses, cardioversion/defibrillation shocks, neurostimulation pulses, or other pulses, such as to one or more locations within, near, or even some distance away from the heart. In some examples, lead system 308 additionally includes a device to deliver a pharmaceutical or other substance. In some examples, lead system 308 includes one or more pacing-sensing leads, which can include at least one electrode configured to be placed in or on a heart 301 for sensing a cardiac electrogram signal or for delivering pacing or cardiac resynchronization pulses. In another example, lead system 308 includes one or more neurostimulation-sensing leads, which can include at least one electrode configured to be placed on a nerve of the autonomic nervous system, such as for sensing one or more neural signals or delivering one or more neurostimulation pulses. In another example, lead system 308 includes one or more pacing-sensing leads and one or more neurostimulation-sensing leads, such as to synchronize or otherwise use neurostimulation with pacing or intrinsic activities of heart 301. In various examples, implantable medical device 310 is capable of measuring posture. This can include measuring the orientation of body 302 with respect to a gravitational field or with respect to a surface.

Externally wearable device 306 can similarly be configured for monitoring the posture of a patient, such as with respect to a gravitational field, or to a surface. Also, in some examples, the externally wearable subsystem 307 is capable of monitoring physiological information, such as heart rate. Some examples use band 309 to measure physiological information (e.g., autonomic balance, respiration, pulmonary fluid, cardiac output, preload, weight change, vascular pressure, heart rate, heart rate variability and heart sounds). In certain examples, the externally wearable subsystem 307 is self-powered, but it some examples, it receives power from a wired electrical connection. The location of the externally wearable subsystem 307 depicted in FIG. 3 is an illustrative example of a suitable location, and other locations are possible.

In some examples, external subsystem 385 is a patient management system including a local external device 390, a network 392, and a remote external device 394. Local external device 390 is generally located within the vicinity of one or both of implantable medical device 310 and externally wearable device 306 and communicates with them bidirectionally via telemetry links 380, 382, in various examples. In some examples, remote device 394 is in a remote location and communicates with external device 390 bi-directionally via network 392, thus allowing a user to monitor or treat a patient from a distant location, such as by using a home computer, personal digital assistant, mobile phone or the like to connect to the remote device 394 over the network 392. In another example, external subsystem 385 includes a local external programmer that is configured to communicate with one or both of implantable medical device 310 and externally wearable device 306 bi-directionally via telemetry links 380, 382.

The location of various system functions within system 300 can vary. In some examples, as illustrated in FIG. 3, implantable medical device 310 includes all sensors and associated components needed to provide an indication of wellness based on measurements of posture and physiological indications. Externally wearable subsystem 307, as illustrated, can also include all the sensors and associated components needed to provide a wellness indication, in some configurations. But additional configurations share one or more operational functions between two or more of subsystems 305, 307, and 385. For example, in some examples, a physiological sensor collects information, and transmits it directly to external subsystem 385 for processing a wellness indicator. These configurations are not exhaustive or exclusive, and other configurations are possible.

Figure 4:
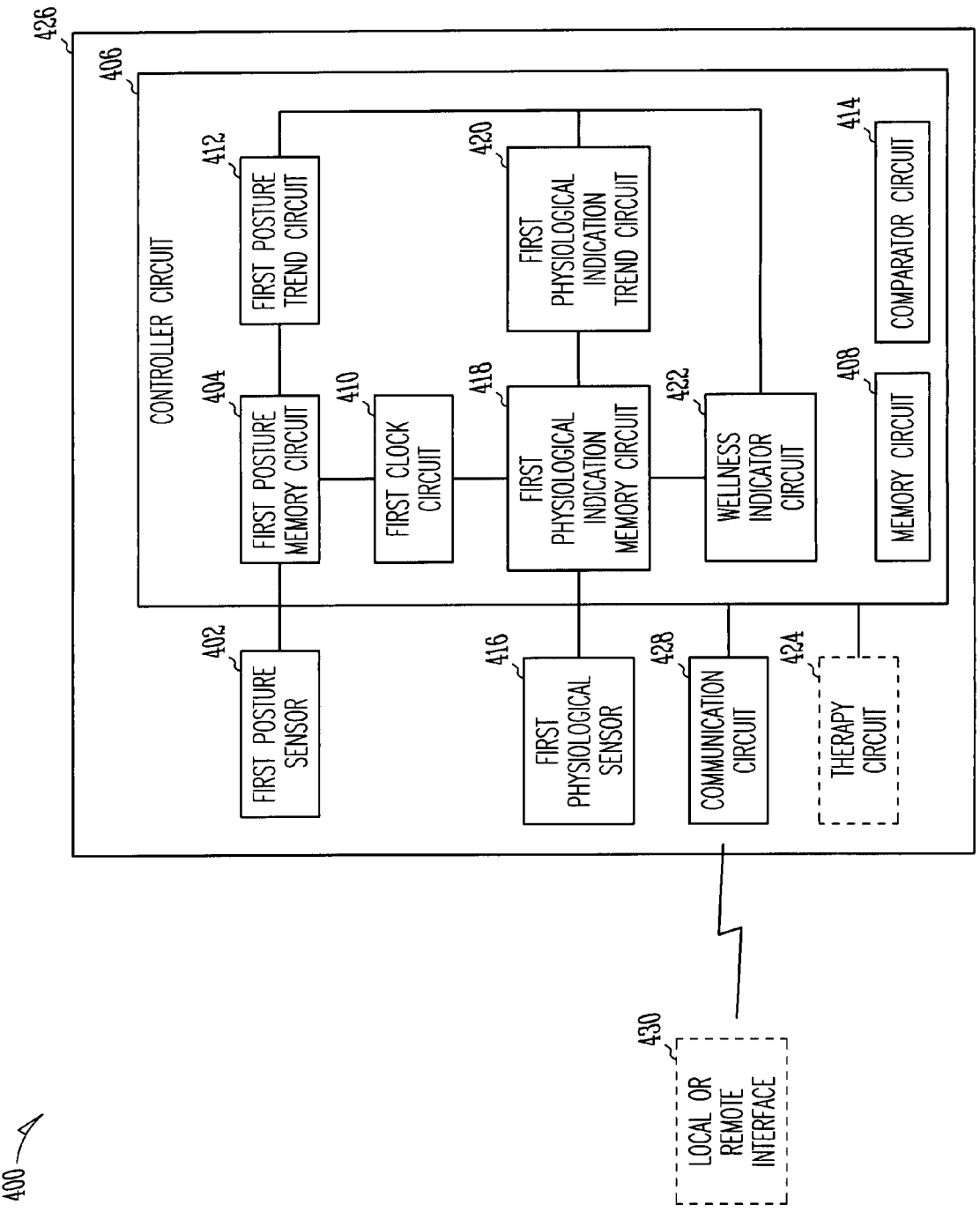
FIG. 4 illustrates a system 400 for posture sensing and for monitoring physiological information, according to some examples.

FIG. 4 illustrates an example of a system 400, such as for posture sensing and for monitoring physiological information. In this example, the system 400 includes a first posture sensor 402 that is configured to indicate one or more postures such as a first lateral decubitus posture (LDP). The first LDP can include a right lateral decubitus posture (RLDP), in which a patient is on his or her right side, or a left lateral decubitus posture (LLDP), in which the patient is on his or her left side. In certain examples, the first posture sensor 402 can distinguish between the RLDP and the LLDP. In certain examples, the first LDP represents only one of the RLDP or the LLDP. In certain examples, the first LDP represents occurrences of either of the RLDP or the LLDP. In some examples, the first posture sensor 402 is configured to indicate one or more additional postures, such as a prone posture or a supine posture. Certain examples can measure an angular degree to which a patient recumbently reclines. Certain examples can measure an angular degree of the LDP (e.g., how perpendicular the patient is to an underlying surface when the patient is lying on his or her side).

In various examples, the first posture sensor 402 produces an electrical signal representing the orientation of the first posture sensor 402 relative to surface or relative to a gravitational field. Examples of a first posture sensor 402 include, but are not limited to, one or more of a tilt switch, a single axis accelerometer, or a multi-axis accelerometer. Various examples can include one or more accelerometers that monitor acceleration, which can be configured such that posture can be inferred from the acceleration. In some examples, the first posture sensor 402 is coupled to a patient who is in a known orientation so that the sensor can be calibrated. Calibration is useful with certain sensors, as implantation orientation can vary from patient to patient, and certain sensors may not be able to discern a reference orientation for a gravitational field without such calibration.

Some examples include a first posture sensor 402, which is coupled to a first posture memory circuit 404. In certain examples, a first posture memory circuit 404 is configured to store posture sensor information in a record. The record can also include other information (e.g., from one or more other physiological sensors) taken at or near the time of the posture measurement. The sensor information can pass directly from the first posture sensor 402 to the first posture memory circuit 404, or it can be conditioned for storage in the first posture memory circuit 404. In various examples, controller circuit 406 is configured to convert the sensor signal into data that can be stored in first posture memory circuit 404.

Controller circuit 406 can include various components. Controller circuit 406, in some examples, includes a single circuit and performs the functions illustrated, but in additional examples, other configurations are used. Circuits of the present examples can be implemented using any suitable combination of hardware and software. For example, one or more elements can be implemented using an application-specific circuit constructed to perform one or more particular functions. Elements are implemented using firmware, in various examples. Some examples use a general-purpose circuit programmed to perform such function(s). Such a general-purpose circuit can include, but is not limited to, a microcontroller or portions thereof, or a programmable logic circuit or a portion thereof. The controller can include a digital signal processor, or other processing components, and can be integrated into a single component or partitioned into more than one component. The controller circuit 406 can include any suitable processing device for applying logical operations to the posture and physiological data. The controller circuit 406 can use memory circuit 408 for programming and storage of received information and processed data while implementing one or more logic operations, in various examples.

For example, a tilt switch can provide a binary on/off signal. Controller circuit 406 can be configured to receive such a signal and to associate it with a posture, in various examples. As such, first posture memory circuit 404 can store posture information instead of binary switch information. Examples can store binary information and perform a conversion when information is extracted from first posture memory circuit 404. When such tilt switches are used, and more than two postures are to be recorded, two or more of such switches can be used. For an accelerometer, a range of signals representing posture can be provided to either the posture memory circuit 404 or to the controller circuit 406 for preconditioning before being stored in the posture memory circuit 404. In various examples, the accelerometer signal can be amplified or filtered before storage, such as to provide a sufficient granularity for more precisely determining the degree of posture of a patient.

In some configurations, the first posture sensor 402 and the first posture memory circuit 404 are mounted on a single printed circuit board or hybrid circuit. In additional examples, the first posture sensor 402 is implanted in a patient, and communicates wirelessly with first posture memory circuit 404. Other variations are possible, including examples in which the first posture memory circuit 404 is implanted, and the first posture sensor 402 is external to a patient.

In various examples, first posture memory circuit 404 stores a record representing one or more postures, in various examples. One or more of a lateral decubitus posture, a supine posture, a prone posture, or another posture can be stored electronically or otherwise in the record.

In various examples, posture data is stored in conjunction with time data produced by the first clock circuit 410. The time information provided by the first clock circuit 410 can allow other circuits to determine how long the patient remains in a particular posture. The first clock circuit 410 can include a simple timer circuit, such as a clock used to drive the operations of one or more circuits, or it can be a more elaborate time keeping device such as a clock that maintains the actual time of day. The first clock circuit 410 provides timing data or pulses to the controller circuit 406, in some examples, and the controller circuit 406 uses these pulses to determine time intervals.

Various examples include a first posture trend circuit 412. In various examples, the posture trend circuit is equipped to perform analysis on information stored in the record of first posture memory circuit 404. First posture trend circuit 412, in various examples, develops a posture trend on information stored in the first posture memory circuit 404. In various examples, the first posture trend circuit 412 provides a trend that includes at least one of a ratio, a histogram, a fitted curve, and other indications of trends. In some examples, first posture trend circuit 412 provides a ratio of time spent in a right lateral decubitus position to time spent in a left lateral decubitus position.

In certain examples, a wellness indication is provided that includes a ratio of the time spent in a right lateral decubitus posture to the time spent in a left lateral decubitus posture. In certain examples, the computation of the ratio or other mathematical relationship may use a comparator circuit 414 that is coupled to or incorporated in the controller circuit 406. For example, this can include calculating a ratio of a physiological signal in a first posture to the physiological signal in a second posture. This ratio can be computed for a healthy person and stored in the memory circuit 408 or an external device. The device 400 calculates a similar ratio for the particular patient in whom the device is implanted, such as by using information received from the first physiological sensor 416 and the first posture sensor 404. These ratios can then be compared at a particular time or over a time period, such as to determine the particular patient's health status, which may include information about improvement or worsening of such health status, particularly with respect to heart failure. In certain examples, the ratio can be calculated as:

$$100*(RLDP/LLDP) \quad (2)$$

In the above equation, RLDP relates to a right lateral decubitus posture, and LLDP relates to a left lateral decubitus posture.

In some examples, the first posture trend circuit 412 populates a histogram with various angles that are measured and represent posture with respect to a surface. Such information can help a physician determine the wellness level of a patient. For example, if there is a slight bias from right lateral decubitus posture to left lateral decubitus posture, it could be overlooked. However, if a physician knew that the patient was indeed spending much more time in a right lateral decubitus posture, but it was not showing up in measurements because the patient was lying tilted slighting out of the right lateral decubitus posture, a histogram that records angles could include such information. Such a histogram, in some examples, includes information representing how long a person spends lying at, for example, 30 degrees with respect to a surface. A fitted curve can be used to store information about posture trend in a smaller memory than would be required to store all of the measured data used to fit the curve. Devices having smaller memory are more comfortable in use, especially when they are implanted.

In various examples, a first physiological sensor 416 detects a first physiological indication for a patient (e.g., autonomic balance, respiration, pulmonary fluid, cardiac output, preload, weight change, vascular pressure, heart rate, heart rate variability and heart sounds), and produces a signal representing that indication. The signal representative of one or more first physiological states is communicated to first physiological indication memory circuit 418 and stored. In various examples, the first physiological indication trend circuit 420 trends such information. If a physiological trend moves away from a specified trend during posture changes, a wellness indication can be associated with that change.

In various examples, a wellness indicator circuit 422 is coupled to the first posture trend circuit 412 and the first physiological indication trend circuit 420. In various examples, the wellness indicator circuit 422 is configured to compute and provide a wellness indication based on one or more trends from these components. A wellness indication is computed, in various examples, by comparing information gathered from the first posture sensor 402 and first physiological sensor 416 to specified information. In some examples, a single value is measured by a sensor and is ultimately compared to a specified value. For example, if the patient is prescribed to sleep only in the right lateral decubitus position, the wellness indicator can provide an alert that the patient is not sleeping in the right lateral decubitus position. In additional examples, multiple values are compared to multiple specified values. In some of these examples, the wellness indicator circuit 422 cross references measured values to specified values using an index such as a time index. In some examples, the wellness indicator includes a specified trend, and compares a trend produced by a trend circuit to that specified trend.

In certain examples, the wellness indicator circuit 422 indicates wellness based on a change in physiological status caused by a change in posture. For example, a normal patient may present a first change in physiological status upon switching from a supine posture to a lateral decubitus posture. A patient with heart failure can experience a second change in physiological status that is different from the first change. Thus, in certain examples, the wellness indicator circuit 422 can compare, using, for example, comparator circuit 414, the patient's response to a change in posture to determine an indication of whether the patient's wellness is static, or is improving or worsening. Such a comparison could include a day over day comparison of a ratio of time spent in a right lateral decubitus posture versus a left lateral decubitus posture, in various examples.

Various examples take such a wellness indicator and use it to control an optional therapy circuit 424. Therapy circuit can provide therapy to the patient based on wellness trends. Examples that include a therapy circuit are configured to provide one or more therapies including, but not limited to, electrical pulse therapy, drug delivery therapy, and neural stimulation therapy, on a feedback basis. Pacing and cardiac resynchronization therapy can be adjusted various ways, such as by changing the rate of the delivered pulses, changing the amplitude of the delivered pulses, changing the pulse width of the delivered pulses, adjusting the location in the patient's heart where the pacing pulses are delivered, adjusting AV-delay, inter-ventricular delay, intra-ventricular delay, or adjusting anti-tachyarrhythmia therapy.

Delivery of one or more stimulation pulses to the autonomic nervous system (ANS) can be controlled in response to a postural change or to a change in one or more physiological signals. For example, if a heart rate variability sensing circuit is provided as part of subsystem 426, and that circuit senses a lesser change in HRV when the patient changes posture, then one or more responsive neurostimulation pulses can be delivered to one or more ANS locations to influence the autonomic balance and obtain a more normal HRV response to posture.

Drug delivery feedback is also possible. For example, if a patient exhibits a smaller heart rate increase upon a posture change, a diuretic or one or more pharmaceuticals can be delivered to patient that relieve pulmonary fluid congestion. In certain examples, a cardiac resynchronization therapy can be additionally initiated or adjusted in an attempt to increase or restore the heart rate increase upon becoming upright.

In the example shown in FIG. 4, the system 400 includes communication circuit 428 that allows the controller circuit 406 to communicate information to a local or remote interface 430. In various examples, the local or remote interface 430 is used by a physician to monitor a patient. In some examples, subsystem 426 employs communication circuit 428 to communicate bi-directionally and wirelessly with a device programmer. The programmer can also communicate back to system 400, such as to update instructions stored in memory circuit 408 that are employed by the controller circuit 406 to bring about one or more logical operations discussed here.

Figure 5:
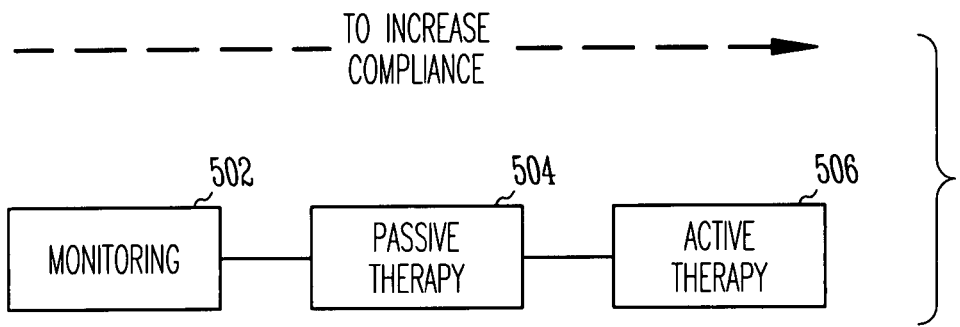
FIG. 5 illustrates a method for monitoring compliance and encouraging compliance to a prescription, according to some examples.

Various examples provide an alert based on a wellness indication. Examples of various alerts are provided in the discussions associated with FIGS. 5-8. FIG. 5 illustrates a diagram for monitoring a patient, including monitoring for lateral decubitus posture, and for treating a patient based on lateral decubitus posture, according to some examples. At 502, a patient is monitored, including monitoring a decubitus posture. At 504, if the patient is not complying with preferred behavioral patterns with respect to a posture, passive therapy is administered, including providing one or more alerts which are easier to ignore. At 506, active treating is administered to the patient. Active treating can include providing an alert or therapy which is less easy to ignore.

Preferred behavioral patterns can be those that are determined to be indicative of wellness, such as by a statistically significant study of multiple patients, in some examples. In additional examples, a preferred behavioral pattern is one that is prescribed by a physician, which can be based on an individualized approach to an individual patient's wellness. Various examples include a preferred behavior pattern which includes spending a significant amount of time in the right lateral decubitus posture.

Figure 6:
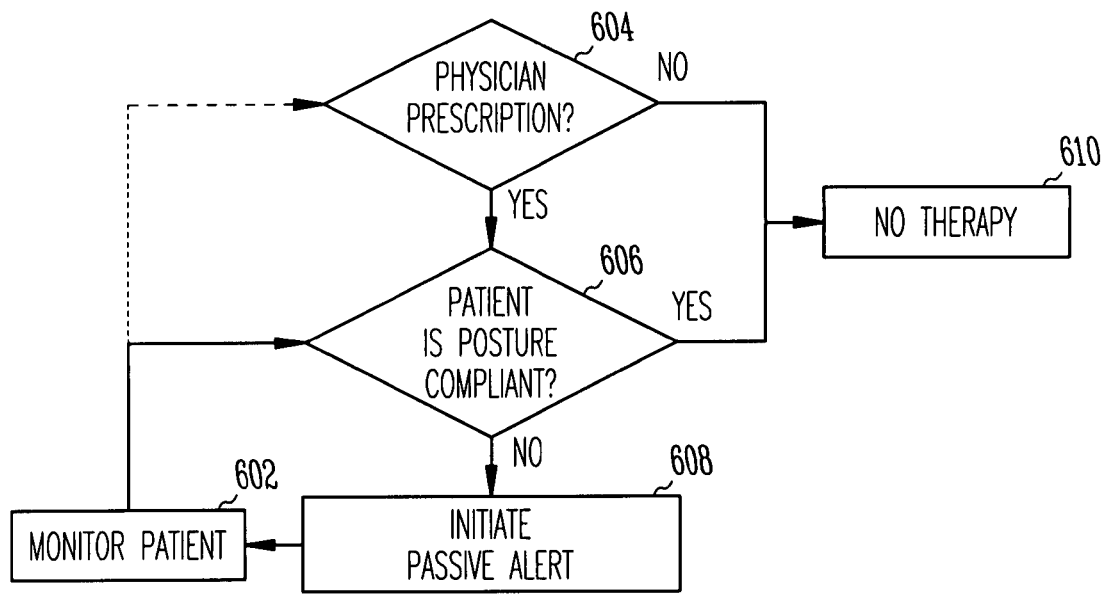
FIG. 6 illustrates a diagram for monitoring compliance and encouraging compliance to a prescription, according to some examples.
Figure 7:
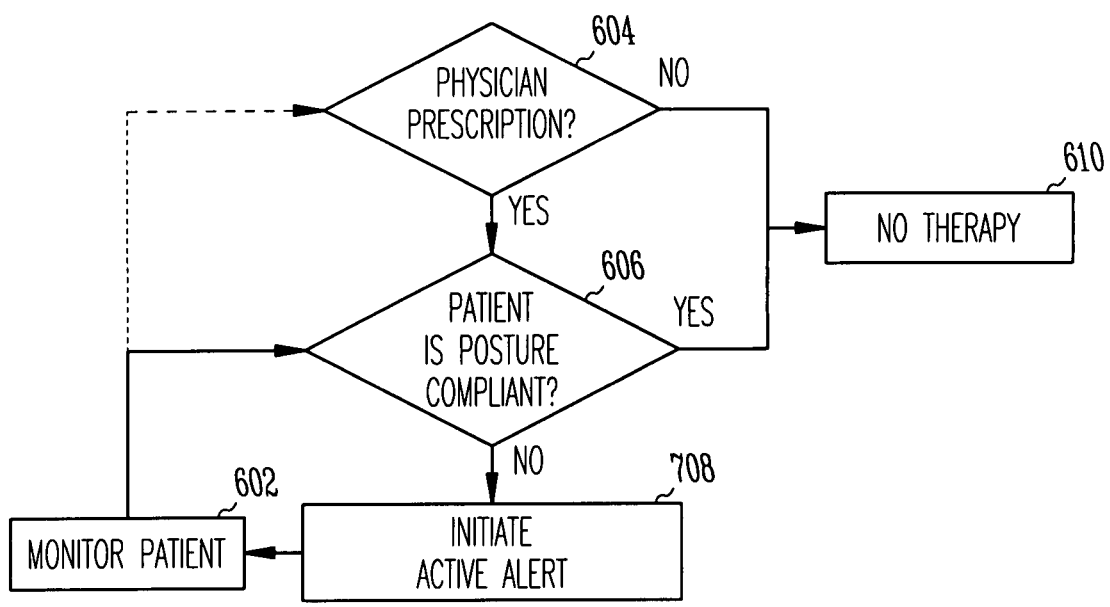
FIG. 7 illustrates a diagram for monitoring compliance and encouraging compliance to a prescription, according to some examples.

FIG. 6 illustrates a diagram for monitoring compliance and encouraging compliance to a prescription, according to some examples. FIG. 7 illustrates a diagram for monitoring compliance and encouraging compliance to a prescription, according to some examples. The illustrated diagrams can be executed within a single device, or can be executed by a combination of devices. The illustrated diagrams can be executed automatically within a device. Execution can take place in real-time, or can be administered along predetermined time periods, such as daily.

Each diagram includes the act of monitoring a patient at 602. Monitoring a patient includes any of the technologies discussed here, including monitoring with internal or external devices, and monitoring physiological indicators (e.g., autonomic balance, respiration, pulmonary fluid, cardiac output, preload, weight change, vascular pressure, heart rate, heart rate variability and heart sounds). The diagram decides at 604 whether a physician has administered a posture prescription to a patient. An example posture prescription can require that a patient assume a posture that is beneficial to their wellness. Whether a patient has such a prescription can be preprogrammed into a device. If there has been no prescription, no therapy is provided at 610. If a posture has been prescribed, the diagram tests whether the patient is compliant with the prescribed posture at 606. If the patient complies with the posture, no therapy is performed at 610. If the patient is not compliant, FIG. 6 diagrams that the patient is subjected to a passive alert at 608. FIG. 7 diagrams that if a patient is not compliant, they are subjected to an active alert at 708. Passive alerts and active alerts are detailed in the discussion associated with FIG. 8.

Figure 8:
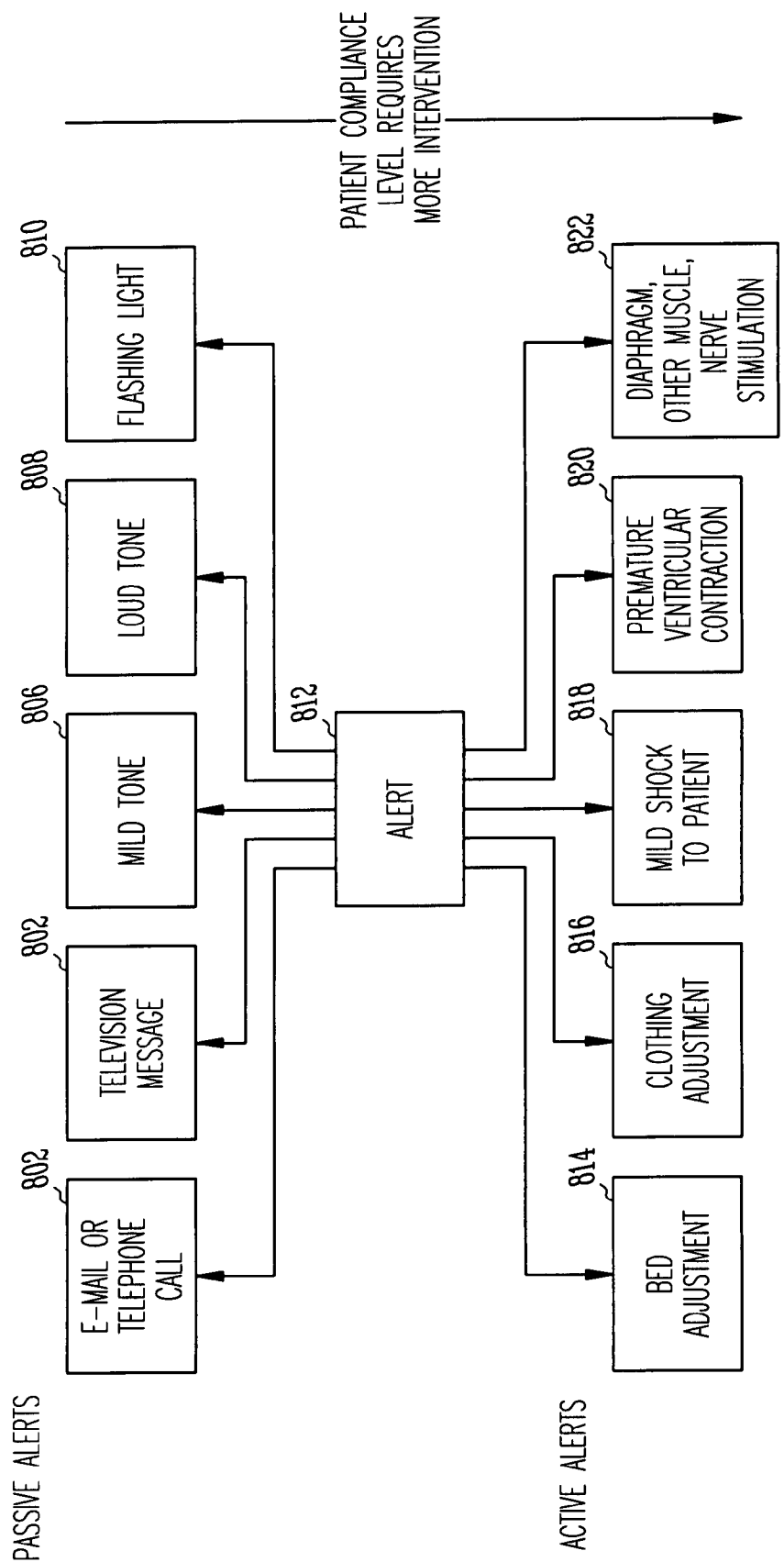
FIG. 8 illustrates an alert and various acts associated with an alert, according to some examples.

FIG. 8 illustrates an alert 812 and various acts associated with an alert 812, according to some examples. A variety of alerts can be provided depending on how compliant a patient is with prescribed therapy. Illustrated are passive alerts that include, but are not limited to, a notification, such as an e-mail or a telephone call 802, a message on a television 804, or a mild tone 806, to something more difficult for a subject to ignore, such as a loud tone 808, or a flashing light 810. Alerts that are active alerts can be provided. These are alerts that are more difficult to ignore, and which are provided when a patient is less compliant with a prescription. These can include, but are not limited to, an adjustment to a bed (e.g. temperature or tilt) 814, an adjustment to something worn by the patient (such as a tightening, pinching or vibrating cuff or a vibrating implanted device) 816, an adjustment to ambient temperature, etc. Some examples provide an active alert that is very difficult to ignore, such as a mild shock 818, vibration, or other energy from an implantable medical device. The shock, vibration, or other energy level can be specified so as to be perceptible to the patient, but not painful. In certain examples, the shock or other energy can be delivered in a manner that causes a premature ventricular contraction (PVC) 820, an intermittent diaphragm stimulation shock, or nerve stimulation (e.g., to cause a muscle twitch, an itch, or a burning sensation, or the like) 822. One or more of these alerts 812 can occur sequentially in a way that gradually encourages a patient to assume a posture, such as a right lateral decubitus posture, or they can occur simultaneous to increase the confidence that a patient will comply with a prescription.

An alert 812 can be provided at a constant intensity level, or can vary in intensity or type over time. For example, an alert 812 that serves as a mild irritant can be configured to grow in intensity until the patient finds it difficult to ignore. Such an escalation can occur parallel to a patient's ongoing failure to comply with a prescription to assume a posture, such as a right lateral decubitus posture, in various examples.

Additional alerts can also be provided. In some examples, an indicator is stored in a memory to indicate a change in wellness. In some examples, an alert 812 is displayed on a display that can be read by a caregiver or other person. Some examples display an alert 812 on a patient display, such that it can be perceived by the patient. For example, in some examples, a patient is reminded of their health status by showing the patient the current state of one or more physiological indications. In some examples, historical or specified physiological indications are also provided to a patient for comparison. In some examples, the alert 812 is provided so that it can be perceived by a physician. Such an alert 812 can be displayed on a programmer for an implantable medical device, in some examples.

In some examples, an alert 812 is provided for use by other devices. For example, in some examples, an implantable medical device is configured to receive an alert 812 and to provide a therapy based on the alert 812. For example, if alert 812 is provided indicating that a patient needs therapy, some examples alter or administer that therapy. Some examples do this automatically. Various examples control optional therapy circuit 422. Some examples alter or administer cardiac rhythm management therapy based on an alert 812.

Figure 9:
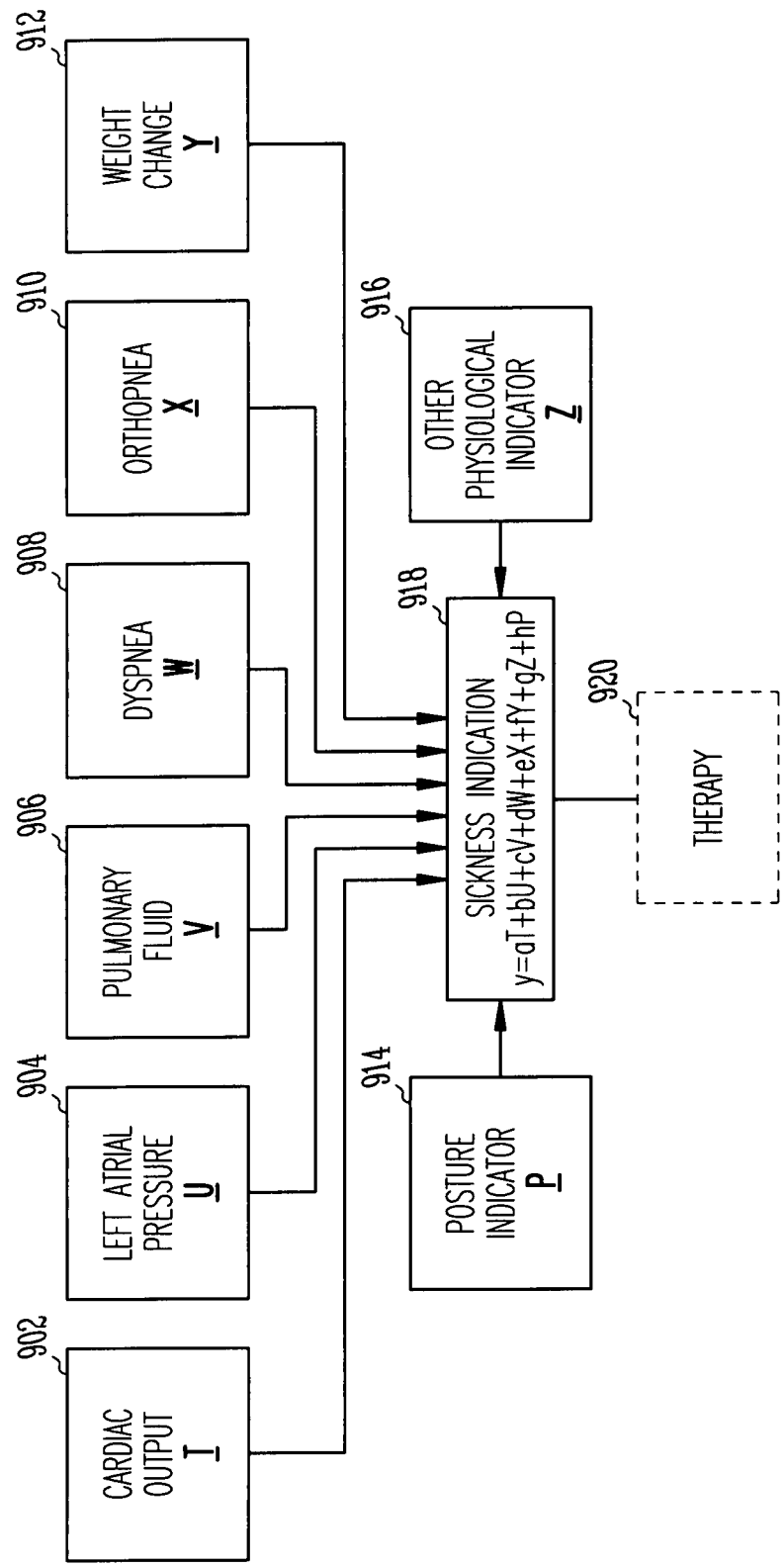
FIG. 9 illustrates a method that includes diagnosing a sickness, according to some examples.

FIG. 9 illustrates a method that includes diagnosing a sickness, according to some examples. The method is capable of monitoring various physiological indicators of a patient. Some examples measure a single indicator, and some examples measure two or more indicators. A cardiac output indication T is recorded, at 902. Left atrial pressure indication U is recorded at 904. Pulmonary fluid indication V is recorded at 906. Dyspnea indication W is recorded at 908. Orthopnea indication X is recorded at 910. Weight change indication Y is recorded at 912. An indication of posture P is recorded at 914. Another physiological indicator Z not expressly indicated here is recorded at 916.

These indicators can be used alone or in aggregate to provide a sickness indicatory at 918. Each of the indications T-Z can be measured in real time (e.g., a pressure reading from a pressure sensor) or can be populated with trend information based on multiple measurements. The sickness indication, in various examples, collects indications T-Z and weights them according to a specified weighting scheme. The weighting scheme can include the example represented by Equation (3).

$$y = aT + bU + cV + dW + eX + fY + gZ + hP \quad (3)$$

If a weighting scheme seeks only to provide a sickness indication that monitors the cardiac output T, the example can assign a weight of 1 to variable a, and a weight of zero to the remaining variables. This weighting scheme can be applied for other variables as well. The weighting can be carried out so that an absolute value of cardiac output T does not affect variable y, the sickness indication, linearly (e.g., $T^2$ could be used, for example). Optionally, it can affect y linearly.

Some systems are tuned to more closely monitor some physiological indicators, such as the occurrence of orthopnea at 910, than variations in left atrial pressure at 904, for example. The sickness indication y can be provided to system 400 as physiological indicator 414 in some examples.

In various examples, if the sickness indication indicates that wellness should be improved with therapy, an alert can be provided. Optionally, a therapy can be provided at 920. The therapy is provided automatically, in some examples. The therapy can include prescribed posture therapy. The therapy can be in a feedback relationship with the sickness indication y, or it can be in an open loop relationship with sickness indication y, requiring a trigger signal based on the sickness indication y.

In some examples, various trends can be recognized, and can be used in providing a sickness indicator. Trends can include information about the time sequence in which various different types of events occur. As more trends are recognized, the degree of confidence that a patient is suffering from a disease or disorder such as heart failure increases, in some examples. Some examples compare a pattern of sequential diagnosed disorders or diseases to a specified trend. One monitors for a pattern which includes, in sequence, decreases in cardiac output, increases in left atrial pressure, increases in sympathetic nerve activity, increases in pulmonary fluid, the appearance of dyspnea (e.g. difficult and labored breathing), the appearance of orthopnea (e.g. difficult or painful breathing except in an erect sitting or standing position), and weight increase. Some examples measure such a sequence, and include an increasing confidence indication that heart failure is present. Other sequences including one or more of these disorders or diseases are possible. Paroxysmal nocturnal dyspnea is additionally monitored, in various examples. Additionally, trepopnea is monitored in some examples.

In various examples, a sickness indication is supplied when a system (e.g., system 400) is polled for a sickness status. In additional examples, a sickness indication is provided automatically once a sufficiently decreased sickness is monitored. Various examples record time durations that are associated with one or more physiological indicators. Some examples provide a sequence of sickness indicators, with each indicator providing updated information. In some examples, successive sickness indications are not provided unless persistent increasing sickness is realized.

Figure 10:
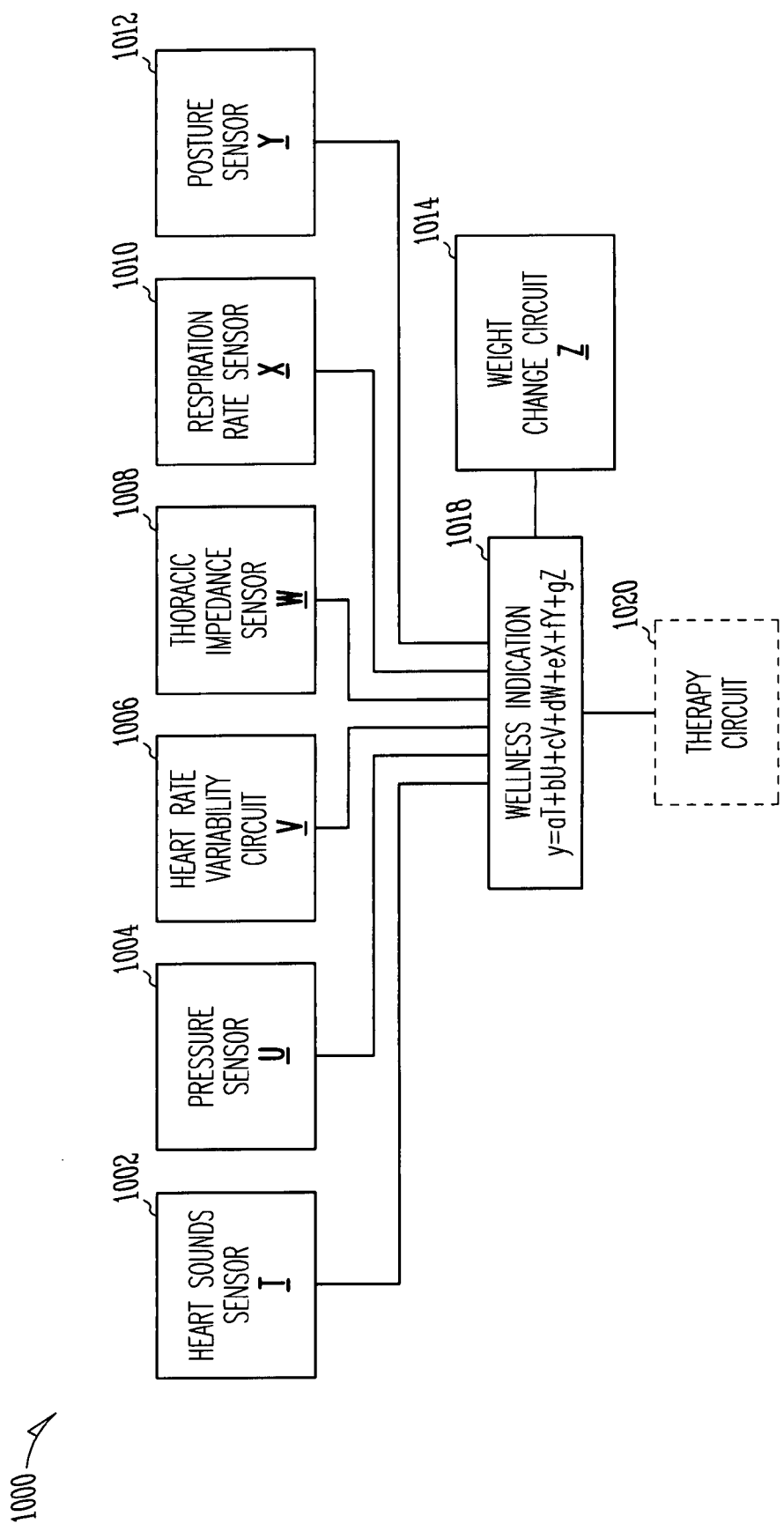
FIG. 10 shows an example of a system, such as for diagnosing a disease, according to some examples.

FIG. 10 shows an example of a system 1000, such as for diagnosing a disease, according to some examples. Included in various examples are one or more devices which can detect physiological indications. Some examples include a heart sounds sensor 1002. Such a sensor can be used to monitor left atrial pressure, in some examples. In various examples, data produced by the heart sounds sensor 1002 is trended, such as by a first physiological indication trend circuit 420. The first physiological indication trend circuit 420 can be used to trend information from devices 1004-1014, in various examples. Various examples additionally implant one or more of the devices 1004-1014. Some examples include a pressure sensor 1004. A pressure sensor can be used to monitor left atrial pressure, in various embodiments. Various examples include a heart rate variability circuit 1006. Such a circuit can be used to measure one or more of heart rate variability, autonomic balance, and heart rate. In some examples, a thoracic impedance sensor 1008 is provided. A thoracic impedance sensor 1008 can be used to measure pulmonary fluid, in some examples. A respiration rate sensor 1010 can be included. Such a sensor can be used to provide information about pulmonary fluid, respiratory rate (e.g. tachypnea), dyspnea and orthopnea. A posture sensor 1012 is provided in some examples. Such a sensor can be used to provide information about dyspnea and orthopnea in some examples, in addition to performing other functions discussed herein. Some examples are capable of monitoring weight change and include a weight change circuit 1014.

These devices can provide one or more indicators T-Z. The indicators can be used alone or in aggregate to provide a wellness indication y 1018. Each of the indications T-Z can be measured in real time (e.g., a pressure reading from a pressure sensor) or can be populated with trend information based on multiple measurements. The sickness indication, in various examples, collects indications T-Z and weights them according to a specified weighting scheme. The weighting scheme can include the example represented by Equation (4).

$$y=aT+bU+cV+dW+eX+fY+gZ \quad (4)$$

If a weighting scheme seeks only to provide a sickness indication that monitors the cardiac output T, the example can assign a weight of 1 to variable a, and a weight of zero to the remaining variables. This weighting scheme can be applied for other variables as well. The weighting can be carried out so that an absolute value of cardiac output T does not affect variable y, the sickness indication, linearly (e.g., $T^2$ could be used, for example). Optionally, it can affect y linearly. The sickness indication can be used to provide therapy produced by a therapy circuit 1020. Therapy circuit 1020 is equivalent to therapy circuit 424 in some examples. The sickness indication y can be provided to system 400 as first physiological indicator 416 in some examples.

Figure 11:
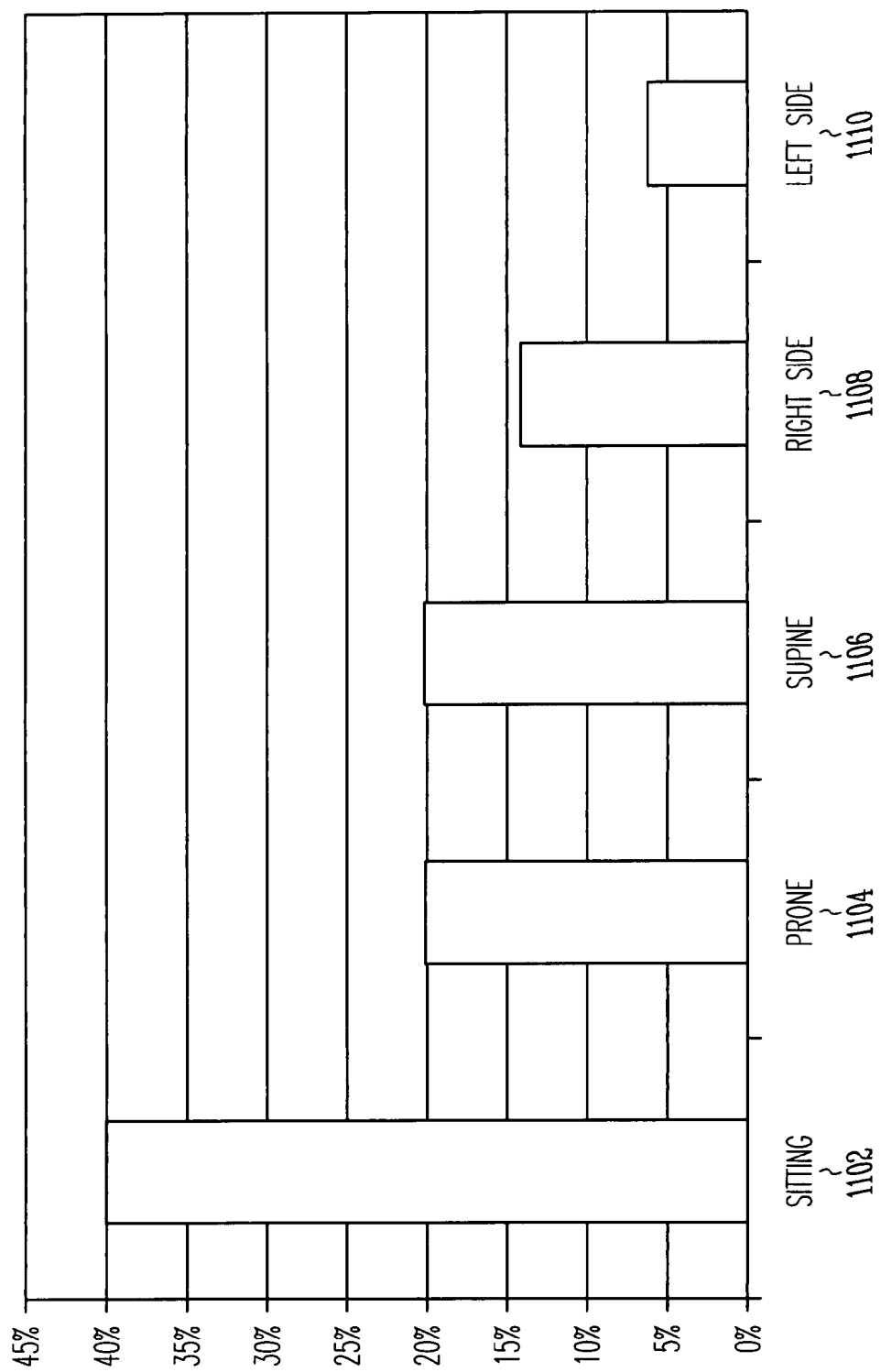
FIG. 11 illustrates data recorded for diagnosis, according to some examples.

FIG. 11 illustrates data recorded or displayed for diagnosis, according to some examples. The illustration shows conceptual recorded patient data. The measurement has recorded percentages of time spent in various postures. Percentage of time spent in a sitting posture is recorded at 1102. Percentage of time spent in a prone posture is recorded at 1104. Percentage of time spent in a supine posture is recorded at 1106. Percentage of time spent in a right lateral decubitus posture is recorded at 1108. Percentage of time spent in a left lateral decubitus posture is shown at 1110. The collection of measurements is stored or displayed as a histogram that can be used by the devices and methods discussed here to provide an indication of wellness or to provide therapy. The histogram is compared to specified values that reflect a desired state of wellness, in some examples.

Such a histogram can be used to record a physiological behavior which demonstrates patient preference. The present techniques can use these measurements to provide a diagnosis that the patient is suffering from heart failure. These measurements can also be used to provide a patient therapy. For example, these measurements demonstrate that the patient is an undesirable amount of time in a left later decubitus posture, and is not spending a preferred amount of time in a right lateral decubitus posture. In various examples, the alerts and other therapies discussed here can be administered accordingly such as to encourage compliance with a prescribed posture. The time spent recording these percentages varies in several examples. Some examples use a 24 hour period. Other examples use a night period, such as 12 midnight to 6 A.M. Some use one sleep cycle. Other time periods are possible.

Figure 12:
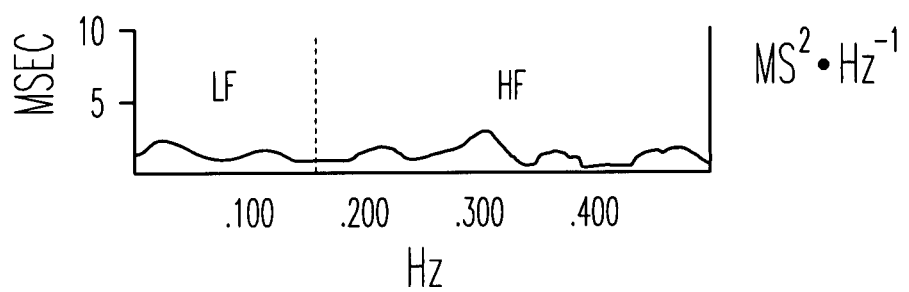
FIG. 12 illustrates data recorded for diagnosis, according to some examples.

FIG. 12 illustrates data recorded or displayed for diagnosis, according to some examples. The illustration shows a conceptual record of heart rate variability. In this example, low frequency (LF) heart rate variability (HRV) is shown and high frequency (HF) heart rate variability is shown. The LF HRV generally includes components of the HRV having frequencies between about 0.04 Hz and 0.15 Hz. The HF HRV generally includes components of the HRV having frequencies between about 0.15 Hz and 0.40 Hz. In some examples, a LF/HF ratio is used to track trends in shifts of autonomic balance. A LF/HF ratio can be provided by a comparator circuit 414, as illustrated in FIG. 4. A substantial change in the LF/HF ratio indicates a change in systemic stress that indicates the degree to which the sympathetic nervous system is activated. With respect to FIG. 4, comparator circuit 414 can provide data to the first physiological indication trend circuit 420 to provide a LF/HF trend, in various examples.

An LF/HF power ratio is derived from the illustrated power spectrum. In some examples, patients with a disease or disorder such as heart failure will have a higher LF/HF ratio than patients who do not. In some examples, patients with a disease or disorder will demonstrate an LF/HF ratio which does not change sufficiently over time. Such an indication can be input into a sickness indication in various examples. This sickness indication can be used in diagnosing patient health, and to provide therapy. The ratio is compared to specified values that reflect a desired state of wellness, in some examples.

FIG. 13 illustrates data recorded or displayed for diagnosis, according to some examples. In this conceptual analysis, five measurements are taken. Measurement 1302 represents time spent in an upright posture. Measurement 1304 represents time spent in a supine posture. Measurement 1306 represents time spent in a right lateral decubitus posture. Measurement 1308 represents time spent in a left lateral decubitus posture. Measurement 1310 represents time spent in any posture. For each measurement, the x-axis is used to track a respiratory rate (e.g., breaths per minute), and the y-axis recorded the number of occurrences of a particular respiratory rate. The five measurements are compiled in combination, but individual measurements are possible. The measurements are compiled concurrently in this example, but it is possible to stagger measurements. The measurements illustrated are recorded from 12 midnight to 6 am, and show that a patient tends to demonstrate a reduced respiratory rate when they spend time in a right lateral decubitus posture.

The measurements can be used to provide wellness indication. For example, a wellness indication can be provided by comparing the measurements to a specified expectation, in various examples. Other examples compare measurements for various postures and provide a wellness indication. For example, the median for measurement 1306 is lower than the median of measurement 1308, which shows that the patient breathing differently in the right lateral decubitus posture versus the left lateral decubitus posture. If this comparison fits a specified pattern, a wellness indication including an actual or potential heart failure diagnosis can be provided, in various examples.

Figure 14:
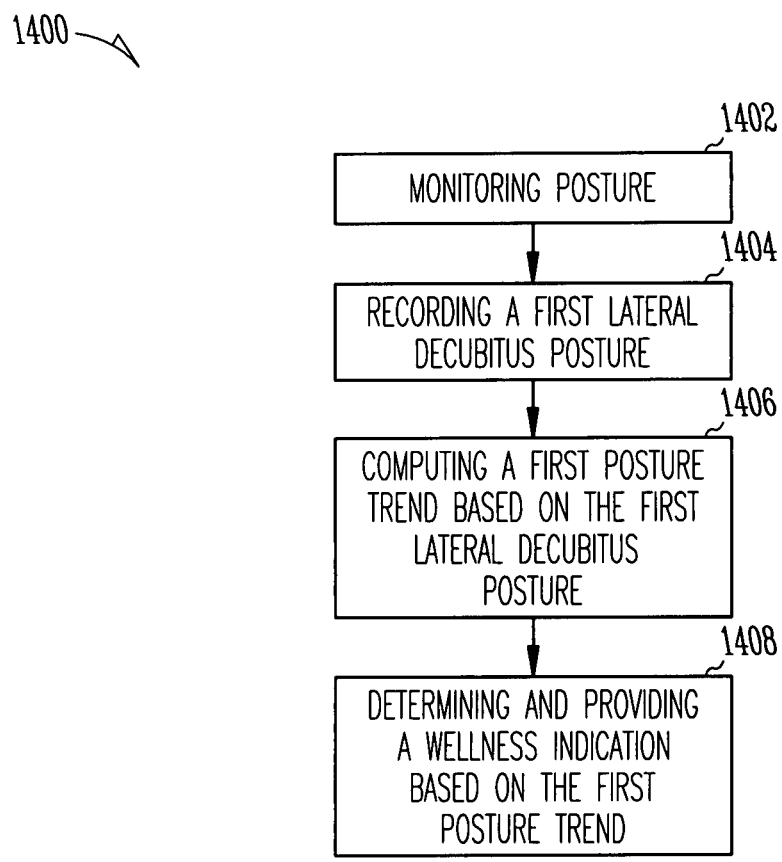
FIG. 14 illustrates a diagram for recording a decubitus posture and providing a wellness indication based on that measurement, according to some examples.

FIG. 14 illustrates a diagram 1400 of an example for providing a wellness indication based on a sensed posture. In this example, at 1402, a posture is monitored. At 1404, a first (e.g., right or left) lateral decubitus posture is recorded. If the device is unable to record any decubitus postures, the device records that failure, in some examples. At 1406, a first posture trend is computed based on the first lateral decubitus posture, in certain examples. At 1408, a wellness indication based on a comparison of the first posture trend to a specified posture trend is determined, in certain examples.

Figure 15:
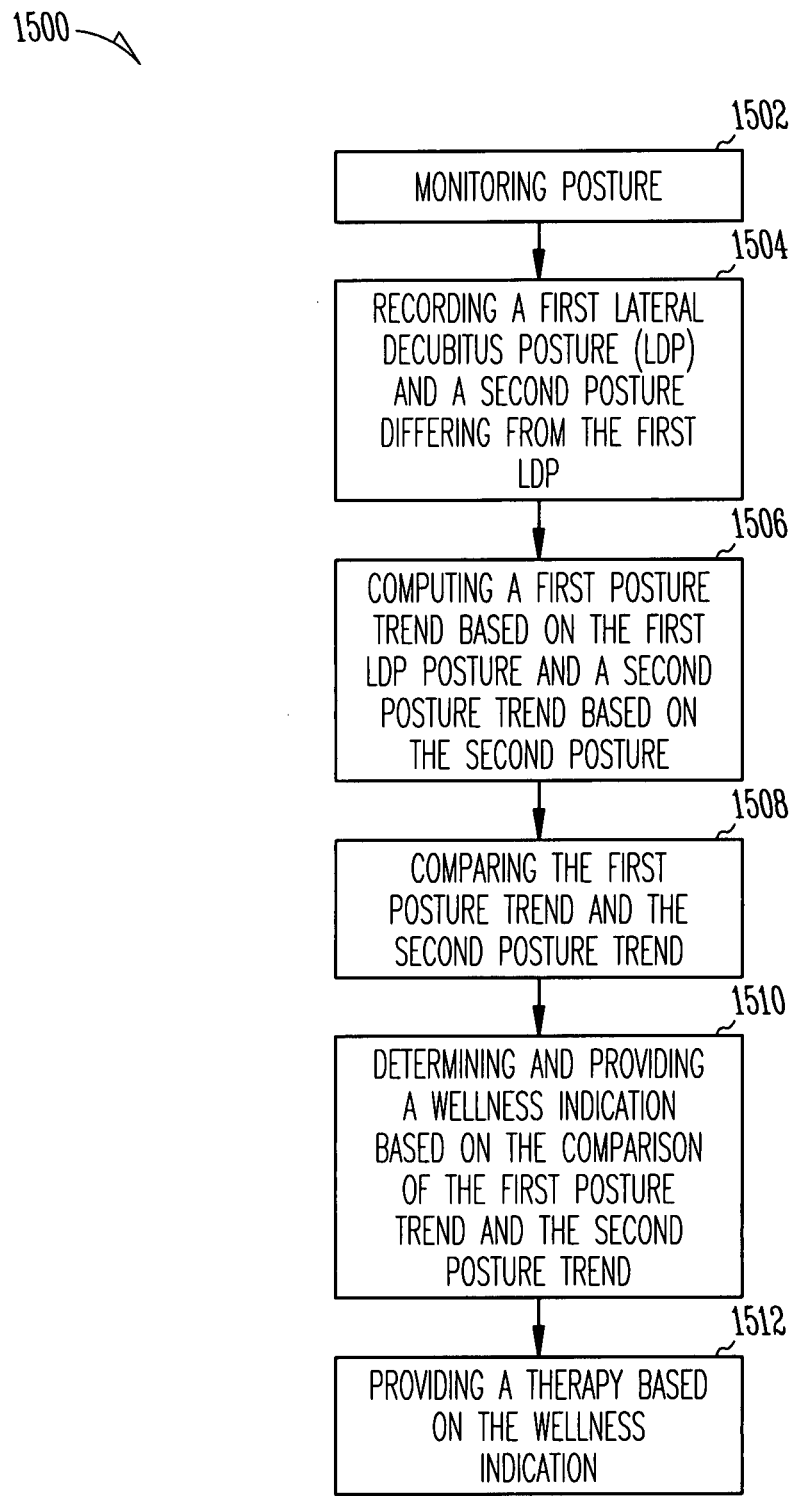
FIG. 15 illustrates a diagram for comparing postures and providing a therapy based on the comparison, according to some examples.

FIG. 15 illustrates a diagram 1500 of an example for comparing postures or providing a therapy ultimately based on the comparison. At 1502, at least two postures are monitored. At 1504, a first lateral decubitus posture, and a second posture differing from the first lateral decubitus posture, are recorded, in certain examples. Postures that differ from the first lateral decubitus posture can include another decubitus posture, in which case the first lateral decubitus posture can represent a right lateral decubitus poster and the second lateral decubitus posture can represent a left lateral decubitus posture. Additional postures that can differ from the first lateral decubitus posture include prone postures and supine postures.

The example computes, at 1506, a first posture trend based on the first lateral decubitus posture and a second posture trend based on the second posture. The example compares the first posture trend and the second posture trend at 1508. The example, at 1510, also determines and provides a wellness indication based on the comparison of the first posture trend and the second posture trend. The example additionally includes, at 1512, providing a therapy based on the wellness indication. In some examples, the therapy provided includes a recommendation of a posture to be assumed so that a patient can experience increased wellness. For example, in some examples, a comparison of a first and a second posture demonstrates that the patient has poor wellness and should assume a supine tilt posture.

Some Notes

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A method of recording posture with an implantable device, the method comprising:
monitoring a right posture signal from an implantable posture sensor in a subject, the right posture signal including a right lateral decubitus posture (LDP) signal;
recording a right LDP record by recording the right LDP signal with a posture memory;
monitoring a left posture signal from the implantable posture sensor, the left posture including a left LDP signal;
recording a left LDP record by recording the left LDP signal with the posture memory;
computing a first posture trend of the subject by periodically comparing the right LDP record and the left LDP record;
comparing the first posture trend to a specified posture-based therapy for heart failure to determine whether the first posture trend is indicative of a change in wellness and automatically providing:
a wellness indication of the change in wellness; and
generating at least one alert indicative of non-compliance of the first posture trend with the specified posture-based therapy, wherein the at least one alert is one of a plurality of escalating alerts provided to the subject to promote compliance with the specified posture-based therapy, wherein the plurality of alerts are of different types that escalate in difficulty to ignore according to a degree of non-compliance with the specified posture-based therapy.

2. The method of claim 1, comprising:
detecting a physiological indication other than posture; and
automatically computing the wellness indication also based on the physiological indication.

3. The method of claim 1, where the wellness indication includes an actual or potential heart failure indication.

4. The method of claim 1, where the first posture trend is recorded over one circadian rhythm period.

5. The method of claim 1, comprising:
recording a further posture differing from the left LDP and right LDP;
computing a second posture trend based on the second posture; and
determining and automatically providing the wellness indication based on the first posture trend and the second posture trend.

6. The method of claim 5, comprising comparing the first posture trend to the second posture trend and determining and providing the wellness indication based on the comparison of the first posture trend and the second posture trend.

7. The method of claim 5, where the further posture includes a supine posture.

8. The method of claim 5, where the further posture includes at least one of a supine posture or a prone posture.

9. The method of claim 5, including providing the at least one alert of the plurality of escalating alerts when the wellness indication includes a decreased wellness indication.

10. The method of claim 1, comprising:
computing the wellness indication based on the right posture and the left posture, the wellness indication including a first wellness level based on the right posture and a second wellness level based on the left posture;
comparing the first wellness level and the second wellness level to determine a further posture associated with increased wellness over the right and left postures; and
providing an indication of the further posture.

11. The method of claim 10, where the further posture includes a supine tilt posture.

12. An apparatus, comprising:
an implantable medical device configured to be implanted in a subject, the implantable medical device comprising:
an implantable posture sensor configured to be implanted in a subject to produce a left posture indication including a left lateral decubitus posture (LDP) and a right posture indication including a right LDP;
a posture memory circuit coupled to the implantable posture sensor, the posture memory circuit configured to store a left LDP record of time spent in the left LDP using the left posture indication and a right LDP record of further time spent in the right LDP using the right posture indication;
a posture trend circuit coupled to the posture memory circuit, the posture trend circuit configured to produce a posture trend of the subject over multiple periods of time using a signal from a comparator circuit, the comparator circuit to compare the left LDP record and the right LDP record;
a wellness indicator circuit coupled to the posture trend circuit, the wellness indicator circuit configured to compare the first posture trend to a specified posture-based therapy for heart failure to determine whether the first posture trend is indicative of a change in wellness and automatically compute and provide a wellness indication of the change in wellness; and
an alert circuit configured to generate at least one alert indicative of non-compliance of the first posture trend with the specified posture-based therapy, wherein the at least one alert is one of a plurality of escalating alerts provided to the subject to promote compliance with the specified posture-based therapy, wherein the plurality of alerts are of different types that escalate in difficulty to ignore according to a degree of non-compliance with the specified posture-based therapy.

13. The apparatus of claim 12, where the posture sensor is configured to produce a supine posture indication, the posture memory circuit is configured to store a supine record based on the supine posture indication, and the posture trend circuit is configured to produce the posture trend based on a comparison of the left LDP record, the right LDP record and the supine record.

14. The apparatus of claim 12, where the posture sensor is an implantable multi-axis accelerometer.

15. The apparatus of claim 12, where the implantable posture sensor is configured to produce a prone posture indication including at least one of a supine posture or a prone posture, the posture memory circuit is configured to store a supine record and a prone record, the prone record and the supine record based on the prone posture indication, and the posture trend circuit is configured to produce the posture trend based on a comparison of the left LDP record, the supine record and the prone record.

16. The apparatus of claim 12, where the wellness indicator circuit is configured to compare the posture trend to a specified posture trend.

17. The apparatus of claim 16, wherein the alert circuit is configured to trigger the at least one alert of the plurality of escalating alerts when the wellness indication includes a decreased wellness indication, wherein the plurality of escalating alerts includes at least one passive alert and at least one active alert triggered according to the wellness indication.

18. The apparatus of claim 17, wherein the at least one passive alert includes at least one of an email message, a phone call, a flashing light, a mattress tilt adjustment signal, a mattress temperature adjustment signal, a mattress firmness adjustment signal, or an audible tone.

19. The apparatus of claim 17, comprising an electrical pulse circuit coupled to the alert circuit, the electrical pulse circuit configured to provide an electrical pulse to the subject as the at least one active alert.

20. The apparatus of claim 19, where the electrical pulse circuit is configured to produce at least one of a premature ventricular complex (PVC), an intermittent diaphragm stimulation, or an uncomfortable electric shock.

21. The apparatus of claim 12, comprising:
a physiologic sensor configured to produce a physiologic indication other than posture;
a physiologic indication memory, coupled to the physiologic sensor, the physiologic indication memory configured to store a physiologic indication record based on the physiology indication; and
a physiologic indication trend circuit coupled to the physiologic indication memory circuit, the physiologic indication trend circuit configured to produce a physiologic indication trend based on the physiologic indication record,
wherein the wellness circuit is configured to compute the wellness indication based on the physiologic record.

22. The apparatus of claim 21, where the physiologic sensor includes, and uses for forming the physiologic indication, at least one of an autonomic balance sensor, a breath sensor, an pulmonary fluid sensor, a cardiac output sensor, a preload circuit, a weight change sensor, a pressure sensor, a heart rate sensor, a heart rate variability sensor, or a heart sounds sensor.

23. The apparatus of claim 22, where the autonomic balance sensor includes a heart rate variability power spectrum comparator configured to produce a ratio of low frequency autonomic activity to high frequency autonomic activity associated with the posture trend.

24. The apparatus of claim 22, where the physiologic indication includes at least one of a paroxysmal nocturnal dyspnea indication or an orthopnea indication.

25. A system for monitoring a patient with an implantable device, the system comprising:
an implantable posture sensor configured to be implanted in the patient to produce a left posture signal including a left lateral decubitus posture (LDP) and a right posture signal including a right LDP;
means for recording a record of the left posture signal and a further record of the right posture signal, including recording a time spent in the right LDP and a further time spent in a left LDP;
means for computing a posture trend of the patient over multiple periods of time by comparing the record of the left posture signal and the further record of the right posture signal, including, for each time period, comparing the time spent in the right LDP to the record of the time spent in the left LDP;
means for comparing the first posture trend to a specified posture-based therapy for heart failure to determine whether the first posture trend is indicative of a change in wellness and for determining and automatically providing a wellness indication based on the change in wellness; and
an alert circuit configured to generate at least one alert indicative of non-compliance of the first posture trend with the specified posture-based therapy, wherein the at least one alert is one of a plurality of escalating alerts provided to the subject to promote compliance with the specified posture-based therapy, wherein the plurality of alerts are of different types that escalate in difficulty to ignore according to a degree of non-compliance with the specified posture-based therapy.

26. The system of claim 25, where the means for monitoring patient posture include a single axis accelerometer.

27. The system of claim 26, where the means for recording a lateral decubitus posture (LDP) include a posture memory circuit coupled to the posture sensor, the posture memory circuit configured to store an LDP record based on the left posture indication.

28. The system of claim 27, where the means for computing a posture trend based on the LDP include a posture trend circuit coupled to the posture memory circuit, the posture trend circuit configured to produce a posture trend based on the LDP record.

29. The system of claim 28, where the means for determining a wellness indication based on the posture trend include a wellness indicator circuit coupled to the posture trend circuit, the wellness indicator circuit configured to compute and provide a wellness indication based on the posture trend.

* * * * *